US007576091B2

(12) United States Patent
McInnes et al.

(10) Patent No.: US 7,576,091 B2
(45) Date of Patent: Aug. 18, 2009

(54) THIAZOLO-, OXAZALO AND IMIDAZOLO-QUINAZOLINE COMPOUNDS CAPABLE OF INHIBITING PROTEIN KINASES

(75) Inventors: Campbell McInnes, Dundee (GB); Mark Peter Thomas, Dundee (GB); Shudong Wang, Nottingham (GB); Neil McIntyre, Angus (GB); Nicholas Westwood, Dundee (GB); Peter Martin Fischer, Arbroath (GB)

(73) Assignee: Cyclacel Limited, Dundee (GB)

( * ) Notice: Subject to any disclaimer, the term of this patent is extended or adjusted under 35 U.S.C. 154(b) by 0 days.

(21) Appl. No.: 11/326,805

(22) Filed: Jan. 6, 2006

(65) Prior Publication Data

US 2006/0264628 A1   Nov. 23, 2006

Related U.S. Application Data

(63) Continuation of application No. PCT/GB2004/002935, filed on Jul. 7, 2004.

(30) Foreign Application Priority Data

Jul. 8, 2003 (GB) ................................. 0315966.2

(51) Int. Cl.
| | | |
|---|---|---|
| *A01N 43/54* | (2006.01) | |
| *A61K 31/505* | (2006.01) | |
| *C07D 239/00* | (2006.01) | |
| *C07D 471/00* | (2006.01) | |
| *C07D 487/00* | (2006.01) | |
| *C07D 491/00* | (2006.01) | |

(52) U.S. Cl. ..................... 514/267; 544/250; 544/251
(58) Field of Classification Search ............... 514/267; 544/250, 251
See application file for complete search history.

(56) References Cited

U.S. PATENT DOCUMENTS

| 5,679,683 | A | 10/1997 | Bridges et al. |
|---|---|---|---|
| 6,531,479 | B2 | 3/2003 | Wang |
| 2003/0055068 | A1 | 3/2003 | Bebbington |

OTHER PUBLICATIONS

Liu, M.C., et al., Novel Strategies in Cancer Therapeutics: Targeting Enzymes Involved in Cell Cycle Regulation and Cellular Proliferation, Current Cancer Drug Targets, 4, 403-424 (2004).*
Mani, et al., Cyclin-dependent Kinase Inhibitors: Novel Anticancer Agents, Exp. Opin. Invest. Drugs 9(8), 1849-70 (2000).*
Meijer, L., et al., Roscovitine and Other Purines as Kinase Inhibitors. From Starfish Oocytes to Clinical Trials, Acc. Chem. Res., 36, 417-425 (2003).*
Noble, M., Protein Kinase Inhibitors: Insights into Drug Design from Structure, Science, vol. 303, Issue 5665, 1800-1805 (2004).*

ATCC No. CCL-185 retrieved online at http://www.atcc.org/ATCCAdvancedCatalogSearch/ProductDetails/tabid/452/Default.aspx?ATCCNum=CCL-185&Template=cellBiology (2008).
ATCC No. HTB-38 retrieved online at http://www.atcc.org/ATCCAdvancedCatalogSearch/ProductDetails/tabid/452/Default.aspx?ATCCNum=HTB-38&Template=cellBiology (2008).
ATCC No. HTB-85 retrieved online at http://www.atcc.org/ATCCAdvancedCatalogSearch/ProductDetails/tabid/452/Default.aspx?ATCCNum=HTB-85&Template=cellBiology (2008).

(Continued)

*Primary Examiner*—James O Wilson
*Assistant Examiner*—Erich A Leeser
(74) *Attorney, Agent, or Firm*—Lahive & Cockfield, LLP; Cynthia L. Kanik; Brian C. Trinque

(57) ABSTRACT

A compound of formula 1, or a pharmaceutically acceptable salt thereof, wherein:

X is S, O, or NH; "a" is a single bond; or "a" is a double bond and one of $R^3$ and $R^4$, and one of $R^5$ and $R^6$ are absent; $R^1$ is H; or is selected from an alkyl group, a cycloalkyl group, a heteroaryl group, an aralkyl group, CO-alkyl, $SO_2$-alkyl, $CO_2R^{13}$ and an aryl group, each of which optionally contains one or more heteroatoms, and is optionally substituted with one or more groups selected from $R^8$ and $R^9$; $R^2$ is H, $R^8$, or an alkyl group optionally substituted with one or more $R^8$ groups; $R^3$, $R^4$, $R^5$, and $R^6$ are each independently selected from H, $R^8$, an alkyl group and an alkenyl group, wherein said alkyl and alkenyl groups are optionally substituted with one or more $R^8$ groups; or $R^3$ and $R^4$, and/or $R^5$ and $R^6$ together represent =O; $R^7$ is H, $R^8$, $NH(CH_2)_nR^9$, $CO(CH_2)_nR^9$, $NHCO(CH_2)_nR^9$, $O(CH_2)_nR^9$, or an alkyl or phenyl group, each of which is optionally substituted with one or more groups selected from $R^8$ and $R^9$; $R^8$ is $OR^{10}$, $NR^{10}R^{11}$, halogen, $CF_3$, $NO_2$, $COR^{10}$, CN, $COOR^{10}$, $CONR^{10}R^{11}$, $SO_2R^{10}$ or $SO_2NR^{10}R^{11}$; $R^9$ is a saturated or unsaturated 5- or 6-membered cyclic group optionally containing one or more heteroatoms selected from N, O and S, and optionally substituted with one or more $R^8$ groups; $R^{10}$, $R^{11}$, $R^{12}$ and $R^{13}$ are each independently H or a hydrocarbyl group; and n is 0, 1, 2 or 3.

Further aspects of the invention relate to pharmaceutical compositions comprising compounds of formula 1, and the therapeutic use thereof in the treatment of proliferative disorders, viral disorders, CNS disorders, diabetes, stroke and cardiovascular disorders.

17 Claims, No Drawings

OTHER PUBLICATIONS

Newell, "Review of Clinical Trials with Cell Cycle Based Strategies," *Clinical Cancer Research*, vol. 7(Suppl.):3822s, No. P825 (2001).

Wu, Su Ying et al., "Discovery of a Novel Family of CDK Inhibitors with the Program LIDAEUS: Structural Basis for Ligand-Induced Disordering of the Activation Loop," *Structure*, vol. 11:399-410 (2003).

Showalter, H.D. Hollis et al., "Tyrosine Kinase Inhibitors. 16. 6,5,6-Tricyclic Benzothieno[3,2-*d*]pyrimidines and Pyrimido[5,4-*b*]- and -[4,5-*b*]indoles as Potent Inhibitors of the Epidermal Growth Factor Receptor Tyrosine Kinase," *J. Med. Chem.*, vol. 42:5464-5474 (1999).

International Search Report for Application No. PCT/GB2004/002935, dated Oct. 5, 2004.

* cited by examiner

THIAZOLO-, OXAZALO AND IMIDAZOLO-QUINAZOLINE COMPOUNDS CAPABLE OF INHIBITING PROTEIN KINASES

RELATED APPLICATIONS

This application is a continuation of PCT/GB2004/002935, filed on Jul. 7, 2004; which claims priority to GB 0315966.2, filed on Jul. 8, 2003. The entire contents of each of these applications are hereby incorporated herein by reference.

BACKGROUND TO THE INVENTION

In eukaryotes, all biological functions, including DNA replication, cell cycle progression, energy metabolism, and cell growth and differentiation, are regulated through the reversible phosphorylation of proteins. The phosphorylation state of a protein determines not only its function, subcellular distribution, and stability, but also what other proteins or cellular components it associates with. The balance of specific phosphorylation in the proteome as a whole, as well as of individual members in a biochemical pathway, is thus used by organisms as a strategy to maintain homeostasis in response to an ever-changing environment. The enzymes that carry out these phosphorylation and dephosphorylation steps are protein kinases and phosphatases, respectively.

The eukaryotic protein kinase family is one of the largest in the human genome, comprising some 500 genes [1,2]. The majority of kinases contain a 250-300 amino acid residue catalytic domain with a conserved core structure. This domain comprises a binding pocket for ATP (less frequently GTP), whose terminal phosphate group the kinase transfers covalently to its macromolecular substrates. The phosphate donor is always bound as a complex with a divalent ion (usually $Mg^{2+}$ or $Mn^{2+}$). Another important function of the catalytic domain is the binding and orientation for phosphotransfer of the macromolecular substrate. The catalytic domains present in most kinases are more or less homologous.

A wide variety of molecules capable of inhibiting protein kinase function through antagonising ATP binding are known in the art [3-7]. By way of example, the applicant has previously disclosed 2-anilino-4-heteroaryl-pyrimidine compounds with kinase inhibitory properties, particularly against cyclin-dependent kinases (CDKs) [8-12]. CDKs are serine/threonine protein kinases that associate with various cyclin subunits. These complexes are important for the regulation of eukaryotic cell cycle progression, but also for the regulation of transcription [13,14].

The present invention seeks to provide new so-called "constrained" heteroaryl-substituted pyrimidine derivatives, in which free rotation of the heteroaryl substituent is hindered. More specifically, the invention relates to 4,5-dihydro-thiazolo-, oxazolo-, and imidazolo-[4,5-h]quinazolin-8-ylamines that have broad therapeutic applications in the treatment of a number of different diseases and/or that are capable of inhibiting one or more protein kinases.

STATEMENT OF INVENTION

The present invention relates to constrained thiazolo-, oxazolo-, and imidazolo-pyrimidine compounds and their use in therapy. More specifically, but not exclusively, the invention relates to compounds that are capable of inhibiting one or more protein kinases.

A first aspect of the invention relates to compounds of formula 1, or pharmaceutically acceptable salts thereof,

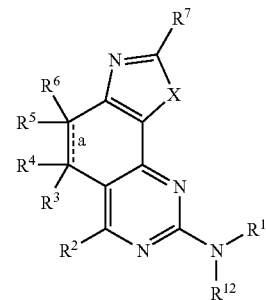

wherein:
X is S, O, or NH;
"a" is a single bond; or
"a" is a double bond and one of $R^3$ and $R^4$, and one of $R^5$ and $R^6$ are absent;
$R^1$ is H; or is selected from an alkyl group, a cycloalkyl group, a heteroaryl group, an aralkyl group, CO-alkyl, $SO_2$-alkyl, $CO_2R^{13}$ and an aryl group, each of which optionally contains one or more heteroatoms, and is optionally substituted with one or more groups selected from $R^8$ and $R^9$;
$R^2$ is H, $R^8$, or an alkyl group optionally substituted with one or more $R^8$ groups;
$R^3$, $R^4$, $R^5$, and $R^6$ are each independently selected from H, $R^8$, an alkyl group and an alkenyl group, wherein said alkyl and alkenyl groups are optionally substituted with one or more $R^8$ groups; or
$R^3$ and $R^4$, and/or $R^5$ and $R^6$ together represent =O;
$R^7$ is H, $R^8$, $NH(CH_2)_nR^9$, $CO(CH_2)_nR^9$, $NHCO(CH_2)_nR^9$, $O(CH_2)_nR^9$, or an alkyl or phenyl group, each of which is optionally substituted with one or more groups selected from $R^8$ and $R^9$;
$R^8$ is $OR^{10}$, $NR^{10}R^{11}$, halogen, $CF_3$, $NO_2$, $COR^{10}$, CN, $COOR^{10}$, $CONR^{10}R^{11}$, $SO_2R^{10}$ or $SO_2NR^{10}R^{11}$;
$R^9$ is a saturated or unsaturated 5- or 6-membered cyclic group optionally containing one or more heteroatoms selected from N, O and S, and optionally substituted with one or more $R^8$ groups;
$R^{10}$, $R^{11}$, $R^{12}$ and $R^{13}$ are each independently H or a hydrocarbyl group; and
n is 0, 1, 2 or 3.

A second aspect of the invention relates to a pharmaceutical composition comprising one or more compounds of formula 1 as defined above admixed with a pharmaceutically acceptable diluent, excipient or carrier.

Further aspects of the invention relate to the use of one or more compounds of formula 1 in the preparation of a medicament for treating one or more of the following conditions:
proliferative disorders;
viral disorders;
CNS disorders;
diabetes;
cardiovascular disorders;
stroke; and
alopecia.

Another aspect of the invention relates to a process for preparing compounds of formula 1 as defined above.

Yet another aspect of the invention relates to the use of a compound according to the invention in an assay for identifying further candidate compounds capable of inhibiting one or more of a cyclin dependent kinase, aurora kinase, GSK and a PLK enzyme.

DETAILED DESCRIPTION

Compounds

In a first aspect, the invention relates to to 4,5-dihydro-thiazolo-, oxazolo-, and imidazolo-[4,5-h]quinazolin-8-ylamines of formula 1 as defined above. Fravolini et al disclose the structurally related compound 2-methyl-8-phenyl-4,5-dihydro-thiazolo[4,5-h]quinazoline [15], however, the biological properties of this compound were not elucidated.

As used herein, the term "hydrocarbyl" refers to a saturated or unsaturated, straight-chain, branched, or cyclic group comprising at least C and H that may optionally comprise one or more other suitable substituents. Examples of such substituents may include halo, alkoxy, hydroxy, $CF_3$, CN, amino, nitro or a cyclic group. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain heteroatoms. Suitable heteroatoms will be apparent to those skilled in the art and include, for instance, sulphur, nitrogen, oxygen, phosphorus and silicon. Preferably, the hydrocarbyl group is an aryl or alkyl group.

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl. Suitable substituents include, for example, one or more groups selected from $R^8$ and $R^9$ as defined above.

As used herein, the term "cycloalkyl" refers to a cyclic alkyl group which may be substituted (mono- or poly-) or unsubstituted. Preferably, the cycloalkyl group is a $C_{3-12}$ cycloalkyl group. Suitable substituents include, for example, one or more groups selected from $R^8$ and $R^9$ as defined above.

As used herein, the term "aryl" refers to a $C_{6-12}$ aromatic group which may be substituted (mono- or poly-) or unsubstituted. Typical examples include phenyl and naphthyl etc. Suitable substituents include, for example, one or more groups selected from $R^8$ and $R^9$ as defined above.

The term "aralkyl" is used as a conjunction of the terms alkyl and aryl as given above.

As used herein, the term "heteroaryl" refers to a $C_{3-12}$ aromatic, substituted (mono- or poly-) or unsubstituted group, which comprises one or more heteroatoms. Preferred heteroaryl groups include pyrrole, pyrazole, pyrimidine, pyrazine, pyridine, quinoline, thiophene and furan. Again, suitable substituents include, for example, one or more groups selected from $R^8$ and $R^9$ as defined above.

As used herein, the term "alkenyl" refers to a group containing one or more carbon-carbon double bonds, which may be branched or unbranched, substituted (mono- or poly-) or unsubstituted. Preferably the alkenyl group is a $C_{2-20}$ alkenyl group, more preferably a $C_{2-15}$ alkenyl group, more preferably still a $C_{2-12}$ alkenyl group, or preferably a $C_{2-6}$ alkenyl group, more preferably a $C_{2-3}$ alkenyl group. Suitable substituents include, for example, one or more groups selected from $R^8$ and $R^9$ as defined above.

One preferred embodiment of the invention relates to compounds of formula 1a, or pharmaceutically acceptable salts thereof, wherein:

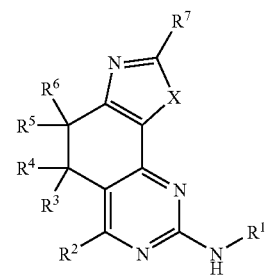

1a

X is S, O, or NH;

$R^1$ is H, an alkyl group, a cycloalkyl group, a heteroaryl group or an aryl group, wherein said alkyl, cycloalkyl, heteroaryl or aryl group optionally contains one or more heteroatoms, and is optionally substituted with one or more groups selected from $R^8$ and $R^9$;

$R^2$ is H, $R^8$, or an alkyl group optionally substituted with one or more $R^8$ groups;

$R^3$, $R^4$, $R^5$, and $R^6$ are each independently selected from H, $R^8$, an alkyl group and an alkenyl group, wherein said alkyl and alkenyl groups are optionally substituted with one or more $R^8$ groups; or $R^3$ and $R^4$, and/or $R^5$ and $R^6$ together represent =O;

$R^7$ is H, $R^8$, $NH(CH_2)_nR^9$, $CO(CH_2)_nR^9$, $NHCO(CH_2)_nR^9$, $O(CH_2)_nR^9$, or an alkyl or phenyl group, each of which is optionally substituted with one or more groups selected from $R^8$ and $R^9$;

$R^8$ is $OR^{10}$, $NR^{10}R^{11}$, halogen, $CF_3$, $NO_2$, $COR^{10}$, CN, $COOR^{10}$, $CONR^{10}R^{11}$, $SO_2R^{10}$ or $SO_2NR^{10}R^{11}$;

$R^9$ is a saturated or unsaturated 5- or 6-membered cyclic group optionally containing one or more heteroatoms selected from N, O and S, and optionally substituted with one or more $R^8$ groups;

$R^{10}$ and $R^{11}$ are each independently H or a hydrocarbyl group; and n is 0, 1, 2 or 3.

In one particularly preferred embodiment of the invention, X is S.

Preferably, $R^{10}$, $R^{11}$ and $R^{12}$ are each independently H or alkyl.

Preferably, $R^{13}$ is alkyl or alkenyl.

In one preferred embodiment, $R^1$ is H, a $C_1$-$C_{12}$ alkyl group, a $C_3$-$C_{12}$ cycloalkyl group, a $C_6$-$C_{12}$ aryl group, or a $C_{3-12}$ heteroaryl group, wherein said alkyl, cycloalkyl, heteroaryl and aryl group optionally contains one, two or three heteroatoms selected from N, O, or S, and is optionally substituted with one, two or three groups selected from $R^8$ and $R^9$.

In another preferred embodiment, $R^1$ is H; or is selected from $CO_2R^{13}$, a $C_1$-$C_{12}$ alkyl group, a $C_3$-$C_{12}$ cycloalkyl group, a $C_6$-$C_{12}$ aryl group, a ($C_1$-$C_{12}$ alkyl)-($C_6$-$C_{12}$ aryl) group, a $C_{3-12}$ heteroaryl group, $SO_2$—($C_6$-$C_{12}$ aryl) and CO—($C_6$-$C_{12}$ aryl), wherein said alkyl, cycloalkyl, heteroaryl and aryl group optionally contains one, two or three heteroatoms selected from N, O, or S, and is optionally substituted with one, two or three groups selected from $R^8$ and $R^9$.

In a more preferred embodiment, $R^1$ is phenyl, pyridin-2-yl, or pyridin-3-yl, each of which may be optionally substituted by one or more substituents selected from $R^8$ and $R^9$.

In another preferred embodiment $R^1$ is H; or is selected from phenyl, pyridin-2-yl, pyridin-3-yl, $CH_2$-phenyl, CO-phenyl, $SO_2$-phenyl, $CO_2$-alkyl and $CO_2$-alkenyl, each of which may be optionally substituted by one or more substituents selected from $R^8$ and $R^9$.

Even more preferably, $R^1$ is a phenyl group optionally substituted by one or more substituents selected from $NO_2$, $CF_3$, OH, morpholino and $NMe_2$.

In another preferred embodiment, $R^1$ is H; or is selected from a phenyl group, CO-phenyl, $SO_2$-phenyl, $CH_2$-phenyl and $CO_2$—$CH_2CH_2CH$=CH, each of which may be optionally substituted by one or more substituents selected from $NO_2$, $CF_3$, OH, morpholino and $NMe_2$.

In one especially preferred embodiment of the invention, $R^1$ is a phenyl group optionally substituted in the 3- or 4-position by a substituent selected from $NO_2$, $CF_3$, OH, morpholino and $NMe_2$.

In another preferred embodiment, $R^1$ is H; or is a phenyl group optionally substituted in the 3- or 4-position by a substituent selected from $NO_2$, $CF_3$, OH, morpholino and $NMe_2$; or $R^1$ is CO-phenyl, $CH_2$-phenyl, $SO_2$-phenyl, or $CO_2$—$CH_2CH_2CH$=CH.

Preferably, $R^2$ is H, $R^8$, or a $C_1$-$C_3$ alkyl group optionally substituted with one or more $R^8$ groups.

In one particularly preferred embodiment, $R^2$ is H.

Preferably, $R^3$, $R^4$, $R^5$, and $R^6$ are each independently selected from H, $R^8$, a $C_1$-$C_3$ alkyl group optionally substituted with one or more $R^8$ groups, and a $C_2$-$C_3$ alkenyl group optionally substituted with one or more $R^8$ groups.

More preferably, $R^2$, $R^3$, $R^4$, $R^5$, and $R^6$ are each independently H or $C_{1-3}$ alkyl optionally substituted by one or more hydroxy groups.

In one particularly preferred embodiment, $R^3$, $R^4$, $R^5$, and $R^6$ are each independently selected from H, $CH_3$, $CH_2OH$ and $CH_2CH_2OH$.

In one especially preferred embodiment of the invention, $R^3$, $R^4$, $R^5$, and $R^6$ are all H.

Preferably, $R^7$ is H, $R^8$, phenyl, $NH(CH_2)_nR^9$, $CO(CH_2)_nR^9$, $NHCO(CH_2)_nR^9$, $O(CH_2)_nR^9$, or a $C_1$-$C_6$ alkyl group optionally substituted with one or more groups selected from $R^8$ and $R^9$.

More preferably, $R^7$ is $C_{1-6}$ alkyl or $R^8$.

In one particularly preferred embodiment, $R^7$ is selected from $CH_3$, $NH_2$, $NHCH_3$, $OCH_3$ and $OCH_2CH_3$.

In one especially preferred embodiment of the invention, $R^7$ is $NH_2$ or $CH_3$.

More preferably, $R^8$ is OH, OMe, OEt, $O^iPr$, $NH_2$, NHMe, $NMe_2$, NHEt, $NH^iPr$, $CF_3$, F, Cl, Br, I, $NO_2$, COMe, COEt, $CO^iPr$, CN, COOH, COOMe, $CONH_2$, CONHMe, $CONMe_2$, $SO_2Me$ or $SO_2NH_2$.

More preferably still, $R^8$ is OH, OMe, OEt, $O^iPr$, $NH_2$, NHMe, $NMe_2$, NHEt, $NH^iPr$, $CF_3$ or $NO_2$.

More preferably, $R^9$ is morpholino.

In one preferred embodiment of the invention, "a" is a single bond.

In another preferred embodiment of the invention, "a" is a double bond, and one of either $R^3$ or $R^4$, together with one of either $R^5$ or $R^6$ are absent.

In one particularly preferred embodiment of the invention, the compound of formula 1 is selected from the following:

(2-Methyl-4,5-dihydro-thiazolo[4,5-h]quinazolin-8-yl)-(3-nitro-phenyl)-amine;
(2-Methyl-4,5-dihydro-thiazolo[4,5-h]quinazolin-8-yl)-(4-trifluoromethyl-phenyl)-amine;
3-(2-Methyl-4,5-dihydro-thiazolo[4,5-h]quinazolin-8-ylamino)-phenol;
(2-Methyl-4,5-dihydro-thiazolo[4,5-h]quinazolin-8-yl)-(4-morpholin-4-yl-phenyl)-amine;
4-(2-Methyl-4,5-dihydro-thiazolo[4,5-h]quinazolin-8-ylamino)-phenol;
N,N-Dimethyl-N'-(2-methyl-4,5-dihydro-thiazolo[4,5-h]quinazolin-8-yl)-benzene-1,4-diamine;
(6-Chloro-pyridin-3-yl)-(2-methyl-4,5-dihydro-thiazolo[4,5-h]quinazolin-8-yl)-amine;
(6-Methoxy-pyridin-3-yl)-(2-methyl-4,5-dihydro-thiazolo[4,5-h]quinazolin-8-yl)-amine;
Methyl-(2-methyl-4,5-dihydro-thiazolo[4,5-h]quinazolin-8-yl)-(3-nitro-phenyl)-amine;
Methyl-(2-methyl-thiazolo[4,5-h]quinazolin-8-yl)-(3-nitro-phenyl)-amine;
(2-Methyl-4,5-dihydro-thiazolo[4,5-h]quinazolin-8-yl)-phenyl-amine;
(2-Methyl-thiazolo[4,5-h]quinazolin-8-yl)-phenyl-amine;
$N^8$-Phenyl-4,5-dihydro-thiazolo[4,5-h]quinazoline-2,8-diamine;
$N^8$-(3-Nitro-phenyl)-4,5-dihydro-thiazolo[4,5-h]quinazoline-2,8-diamine;
2-Methyl-4,5-dihydro-thiazolo[4,5-h]quinazolin-8-ylamine;
N-(2-Methyl-4,5-dihydro-thiazolo[4,5-h]quinazolin-8-yl)-benzamide;
Benzyl-(2-methyl-4,5-dihydro-thiazolo[4,5-h]quinazolin-8-yl)-amine;
(2-Methyl-4,5-dihydro-thiazolo[4,5-h]quinazolin-8-yl)-carbamic acid but-3-enyl ester; and
N-(2-Methyl-4,5-dihydro-thiazolo[4,5-h]quinazolin-8-yl)-benzenesulfonamide.

In an even more preferred embodiment of the invention, the compound of formula 1 is selected from the following:

(2-Methyl-4,5-dihydro-thiazolo[4,5-h]quinazolin-8-yl)-(3-nitro-phenyl)-amine;
(2-Methyl-4,5-dihydro-thiazolo[4,5-h]quinazolin-8-yl)-(4-trifluoromethyl-phenyl)-amine;
3-(2-Methyl-4,5-dihydro-thiazolo[4,5-h]quinazolin-8-ylamino)-phenol;
(2-Methyl-4,5-dihydro-thiazolo[4,5-h]quinazolin-8-yl)-(4-morpholin-4-yl-phenyl)-amine;
4-(2-Methyl-4,5-dihydro-thiazolo[4,5-h]quinazolin-8-ylamino)-phenol;
N,N-Dimethyl-N'-(2-methyl-4,5-dihydro-thiazolo[4,5-h]quinazolin-8-yl)-benzene-1,4-diamine;
(2-Methyl-4,5-dihydro-thiazolo[4,5-h]quinazolin-8-yl)-(4-morpholin-4-yl-phenyl)-amine;
(6-Methoxy-pyridin-3-yl)-(2-methyl-4,5-dihydro-thiazolo[4,5-h]quinazolin-8-yl)-amine;
(6-Chloro-pyridin-3-yl)-(2-methyl-4,5-dihydro-thiazolo[4,5-h]quinazolin-8-yl)-amine;
Methyl-(2-methyl-4,5-dihydro-thiazolo[4,5-h]quinazolin-8-yl)-(3-nitro-phenyl)-amine;
(2-Methyl-4,5-dihydro-thiazolo[4,5-h]quinazolin-8-yl)-phenyl-amine;
(2-Methyl-thiazolo[4,5-h]quinazolin-8-yl)-phenyl-amine;
$N^8$-Phenyl-4,5-dihydro-thiazolo[4,5-h]quinazoline-2,8-diamine; and
$N^8$-(3-Nitro-phenyl)-4,5-dihydro-thiazolo[4,5-h]quinazoline-2,8-diamine.

Highly preferred compounds of the current invention are as follows:
(2-Methyl-4,5-dihydro-thiazolo[4,5-h]quinazolin-8-yl)-(3-nitro-phenyl)-amine,
(2-Methyl-4,5-dihydro-thiazolo[4,5-h]quinazolin-8-yl)-(4-trifluoromethyl-phenyl)-amine,
3-(2-Methyl-4,5-dihydro-thiazolo[4,5-h]quinazolin-8-ylamino)-phenol,
(2-Methyl-4,5-dihydro-thiazolo[4,5-h]quinazolin-8-yl)-(4-morpholin-4-yl-phenyl)-amine,
4-(2-Methyl-4,5-dihydro-thiazolo[4,5-h]quinazolin-8-ylamino)-phenol, and
N,N-Dimethyl-N'-(2-methyl-4,5-dihydro-thiazolo[4,5-h]quinazolin-8-yl)-benzene-1,4-diamine.

In one particularly preferred embodiment, the compounds of the invention are capable of inhibiting one or more of the following protein kinases: CDK1, CDK2, CDK3, CDK4, CDK6, CDK7, CDK8, CDK9, glycogen synthase kinase 3, polo-like kinases, aurora kinases. More preferably still, the compounds are capable of inhibiting one or more of the aforementioned protein kinases at sub-micromolar $IC_{50}$ values.

Therapeutic Use

The compounds of formula 1 have been found to possess anti-proliferative activity and are therefore believed to be of use in the treatment of proliferative disorders such as cancers, leukaemias and other disorders associated with uncontrolled cellular proliferation such as psoriasis and restenosis. As defined herein, an anti-proliferative effect within the scope of the present invention may be demonstrated by the ability to inhibit cell proliferation in an in vitro whole cell assay, for example using any of the cell lines A549, HT29 or Saos-2 Using such assays it may be determined whether a compound is anti-proliferative in the context of the present invention.

On preferred embodiment of the present invention therefore relates to the use of one or more compounds of formula 1 in the preparation of a medicament for treating a proliferative disorder.

As used herein the phrase "preparation of a medicament" includes the use of a compound of formula 1 directly as the medicament in addition to its use in a screening programme for further therapeutic agents or in any stage of the manufacture of such a medicament.

Preferably, the proliferative disorder is a cancer or leukaemia. The term proliferative disorder is used herein in a broad sense to include any disorder that requires control of the cell cycle, for example cardiovascular disorders such as restenosis, cardiomyopathy and myocardial infarction, auto-immune disorders such as glomerulonephritis and rheumatoid arthritis, dermatological disorders such as psoriasis, anti-inflammatory, anti-fungal, antiparasitic disorders such as malaria, emphysema, alopecia, and chronic obstructive pulmonary disorder. In these disorders, the compounds of the present invention may induce apoptosis or maintain stasis within the desired cells as required.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

In one embodiment of the invention, the compound of formula 1 is administered in an amount sufficient to inhibit at least one CDK enzyme.

Preferably, the compound of formula 1 is administered in an amount sufficient to inhibit at least one of CDK2 and/or CDK4.

Another aspect of the invention relates to the use of a compound of formula 1 in the preparation of a medicament for treating a viral disorder, such as human cytomegalovirus (HCMV), herpes simplex virus type 1 (HSV-1), human immunodeficiency virus type 1 (HIV-1), and varicella zoster virus (VZV).

In a more preferred embodiment of the invention, the compound of formula 1 is administered in an amount sufficient to inhibit one or more of the host cell CDKs involved in viral replication, i.e. CDK2, CDK7, CDK8, and CDK9 [23].

As defined herein, an anti-viral effect within the scope of the present invention may be demonstrated by the ability to inhibit CDK2, CDK7, CDK8 or CDK9.

In a particularly preferred embodiment, the invention relates to the use of one or more compounds of formula 1 in the treatment of a viral disorder which is CDK dependent or sensitive. CDK dependent disorders are associated with an above normal level of activity of one or more CDK enzymes. Such disorders preferably associated with an abnormal level of activity of CDK2, CDK7, CDK8 and/or CDK9. A CDK sensitive disorder is a disorder in which an aberration in the CDK level is not the primary cause, but is downstream of the primary metabolic aberration. In such scenarios, CDK2, CDK7, CDK8 and/or CDK9 can be said to be part of the sensitive metabolic pathway and CDK inhibitors may therefore be active in treating such disorders.

Another aspect of the invention relates to the use of compounds of formula 1, or pharmaceutically accetable salts thereof, in the preparation of a medicament for treating diabetes.

In a particularly preferred embodiment, the diabetes is type II diabetes.

GSK3 is one of several protein kinases that phosphorylate glycogen synthase (GS). The stimulation of glycogen synthesis by insulin in skeletal muscle results from the dephosphorylation and activation of GS. GSK3's action on GS thus results in the latter's deactivation and thus suppression of the conversion of glucose into glycogen in muscles.

Type II diabetes (non-insulin dependent diabetes mellitus) is a multi-factorial disease. Hyperglycaemia is due to insulin resistance in the liver, muscles, and other tissues, coupled with impaired secretion of insulin. Skeletal muscle is the main site for insulin-stimulated glucose uptake, there it is either removed from circulation or converted to glycogen. Muscle glycogen deposition is the main determinant in glucose homeostasis and type II diabetics have defective muscle glycogen storage. There is evidence that an increase in GSK3 activity is important in type II diabetes [24]. Furthermore, it has been demonstrated that GSK3 is over-expressed in muscle cells of type II diabetics and that an inverse correlation exists between skeletal muscle GSK3 activity and insulin action [25].

GSK3 inhibition is therefore of therapeutic significance in the treatment of diabetes, particularly type II, and diabetic neuropathy.

It is notable that GSK3 is known to phosphorylate many substrates other than GS, and is thus involved in the regulation of multiple biochemical pathways. For example, GSK is highly expressed in the central and peripheral nervous systems.

Another aspect of the invention therefore relates to the use of compounds of formula 1, or pharmaceutically acceptable salts thereof, in the preparation of a medicament for treating a CNS disorders, for example neurodegenerative disorders.

Preferably, the CNS disorder is Alzheimer's disease.

Tau is a GSK-3 substrate which has been implicated in the etiology of Alzheimer's disease. In healthy nerve cells, Tau co-assembles with tubulin into microtubules. However, in Alzheimer's disease, tau forms large tangles of filaments, which disrupt the microtubule structures in the nerve cell, thereby impairing the transport of nutrients as well as the transmission of neuronal messages.

Without wishing to be bound by theory, it is believed that GSK3 inhibitors may be able to prevent and/or reverse the abnormal hyperphosphorylation of the microtubule-associated protein tau that is an invariant feature of Alzheimer's disease and a number of other neurodegenerative diseases, such as progressive supranuclear palsy, corticobasal degeneration and Pick's disease. Mutations in the tau gene cause inherited forms of fronto-temporal dementia, further underscoring the relevance of tau protein dysfunction for the neurodegenerative process [26].

Another aspect of the invention relates to the use of compounds of formula 1, or pharmaceutically acceptable salts thereof, in the preparation of a medicament for treating bipolar disorder.

Yet another aspect of the invention relates to the use of compounds of formula 1, or pharmaceutically acceptable salts thereof, in the preparation of a medicament for treating a stroke.

Reducing neuronal apoptosis is an important therapeutic goal in the context of head trauma, stroke, epilepsy, and motor neuron disease [27]. Therefore, GSK3 as a pro-apoptotic factor in neuronal cells makes this protein kinase an attractive therapeutic target for the design of inhibitory drugs to treat these diseases.

Yet another aspect of the invention relates to the use of compounds of formula 1, or pharmaceutically acceptable salts thereof, in the preparation of a medicament for treating alopecia.

Hair growth is controlled by the Wnt signalling pathway, in particular Wnt-3. In tissue-culture model systems of the skin, the expression of non-degradable mutants of β-catenin leads to a dramatic increase in the population of putative stem cells, which have greater proliferative potential [28]. This population of stem cells expresses a higher level of non-cadherin-associated β-catenin [29], which may contribute to their high proliferative potential. Moreover, transgenic mice overexpressing a truncated β-catenin in the skin undergo de novo hair-follicle morphogenesis, which normally is only established during embryogenesis. The ectopic application of GSK3 inhibitors may therefore be therapeutically useful in the treatment of baldness and in restoring hair growth following chemotherapy-induced alopecia.

A further aspect of the invention relates to a method of treating a GSK3-dependent disorder, said method comprising administering to a subject in need thereof, a compound of formula 1, or a pharmaceutically acceptable salt thereof, as defined above in an amount sufficient to inhibit GSK3.

Preferably, the compound of formula 1, or pharmaceutically acceptable salt thereof, is administered in an amount sufficient to inhibit GSK3β.

In one embodiment of the invention, the compound of formula 1 is administered in an amount sufficient to inhibit at least one PLK enzyme.

The polo-like kinases (PLKs) constitute a family of serine/threonine protein kinases. Mitotic *Drosophila melanogaster* mutants at the polo locus display spindle abnormalities [30] and polo was found to encode a mitotic kinase [31]. In humans, there exist three closely related PLKs [32]. They contain a highly homologous amino-terminal catalytic kinase domain and their carboxyl termini contain two or three conserved regions, the polo boxes. The function of the polo boxes remains incompletely understood but they are implicated in the targeting of PLKs to subcellular compartments [33,34], mediation of interactions with other proteins [35], or may constitute part of an autoregulatory domain [36]. Furthermore, the polo box-dependent PLK1 activity is required for proper metaphase/anaphase transition and cytokinesis [37, 38].

Studies have shown that human PLKs regulate some fundamental aspects of mitosis [39,40]. In particular, PLK1 activity is believed to be necessary for the functional maturation of centrosomes in late G2/early prophase and subsequent establishment of a bipolar spindle. Depletion of cellular PLK1 through the small interfering RNA (siRNA) technique has also confirmed that this protein is required for multiple mitotic processes and completion of cytokinesis [41].

In a more preferred embodiment of the invention, the compound of formula 1 is administered in an amount sufficient to inhibit PLK1.

Of the three human PLKs, PLK1 is the best characterized; it regulates a number of cell division cycle effects, including the onset of mitosis [42,43], DNA-damage checkpoint activation [44,45], regulation of the anaphase promoting complex [46-48], phosphorylation of the proteasome [49], and centrosome duplication and maturation [50].

Specifically, initiation of mitosis requires activation of M-phase promoting factor (MPF), the complex between the cyclin dependent kinase CDK1 and B-type cyclins [51]. The latter accumulate during the S and G2 phases of the cell cycle and promote the inhibitory phosphorylation of the MPF complex by WEE1, MIK1, and MYT1 kinases. At the end of the G2 phase, corresponding dephosphorylation by the dual-specificity phosphatase CDC25C triggers the activation of MPF [52]. In interphase, cyclin B localizes to the cytoplasm [53], it then becomes phosphorylated during prophase and this event causes nuclear translocation [54,55]. The nuclear accumulation of active MPF during prophase is thought to be important for initiating M-phase events [56]. However, nuclear MPF is kept inactive by WEE1 unless counteracted by CDC25C. The phosphatase CDC25C itself, localized to the cytoplasm during interphase, accumulates in the nucleus in prophase [57-59]. The nuclear entry of both cyclin B [60] and CDC25C [61] are promoted through phosphorylation by PLK1 [43]. This kinase is an important regulator of M-phase initiation.

In one particularly preferred embodiment, the compounds of formula 1 are ATP-antagonistic inhibitors of PLK1.

In the present context ATP antagonism refers to the ability of an inhibitor compound to diminish or prevent PLK catalytic activity, i.e. phosphotransfer from ATP to a macromolecular PLK substrate, by virtue of reversibly or irreversibly binding at the enzyme's active site in such a manner as to impair or abolish ATP binding.

In another preferred embodiment, the compound of formula 1 is administered in an amount sufficient to inhibit PLK2 and/or PLK3.

Mammalian PLK2 (also known as SNK) and PLK3 (also known as PRK and FNK) were originally shown to be immediate early gene products. PLK3 kinase activity appears to peak during late S and G2 phase. It is also activated during DNA damage checkpoint activation and severe oxidative stress. PLK3 also plays an important role in the regulation of microtubule dynamics and centrosome function in the cell and deregulated PLK3 expression results in cell cycle arrest and apoptosis [62]. PLK2 is the least well understood homologue of the three PLKs. Both PLK2 and PLK3 may have additional important post-mitotic functions [35].

In one preferred embodiment, the compound of formula 1 is capable of inhibiting one or more of the following protein kinases at sub-micromolar $IC_{50}$ values: CDK1, CDK2, CDK3, CDK4, CDK6, CDK7, CDK8, CDK9, glycogen synthase kinase 3, polo-like kinases, aurora kinases.

More preferably, said compound of formula 1 exhibits an $IC_{50}$ value for one or more of the above protein kinases of less than 0.1 µM.

Thus, in one preferred embodiment, said compound is selected from the following:
(2-Methyl-4,5-dihydro-thiazolo[4,5-h]quinazolin-8-yl)-(3-nitro-phenyl)-amine;
3-(2-Methyl-4,5-dihydro-thiazolo[4,5-h]quinazolin-8-ylamino)-phenol;
4-(2-Methyl-4,5-dihydro-thiazolo[4,5-h]quinazolin-8-ylamino)-phenol;
N,N-Dimethyl-N'-(2-methyl-4,5-dihydro-thiazolo[4,5-h]quinazolin-8-yl)-benzene-1,4-diamine;
(6-Methoxy-pyridin-3-yl)-(2-methyl-4,5-dihydro-thiazolo[4,5-h]quinazolin-8-yl)-amine;
(6-Chloro-pyridin-3-yl)-(2-methyl-4,5-dihydro-thiazolo[4,5-h]quinazolin-8-yl)-amine;
(2-Methyl-4,5-dihydro-thiazolo[4,5-h]quinazolin-8-yl)-phenyl-amine;
(2-Methyl-thiazolo[4,5-h]quinazolin-8-yl)-phenyl-amine;
$N^8$-Phenyl-4,5-dihydro-thiazolo[4,5-h]quinazoline-2,8-diamine; and
$N^8$-(3-Nitro-phenyl)-4,5-dihydro-thiazolo[4,5-h]quinazoline-2,8-diamine.

More preferably still, said compound of formula 1 exhibits an $IC_{50}$ value for one or more of the above protein kinases of less than 0.01 µM.

Thus, in one preferred embodiment, said compound is selected from the following:
(2-Methyl-4,5-dihydro-thiazolo[4,5-h]quinazolin-8-yl)-(3-nitro-phenyl)-amine;
3-(2-Methyl-4,5-dihydro-thiazolo[4,5-h]quinazolin-8-ylamino)-phenol;
4-(2-Methyl-4,5-dihydro-thiazolo[4,5-h]quinazolin-8-ylamino)-phenol;
(2-Methyl-4,5-dihydro-thiazolo[4,5-h]quinazolin-8-yl)-phenyl-amine;
$N^8$-Phenyl-4,5-dihydro-thiazolo[4,5-h]quinazoline-2,8-diamine; and
$N^8$-(3-Nitro-phenyl)-4,5-dihydro-thiazolo[4,5-h]quinazoline-2,8-diamine.

Even more preferably, said compound of formula 1 exhibits an $IC_{50}$ value for one or more of the above protein kinases of less than 0.001 µM.

Thus, in one preferred embodiment, said compound is $N^8$-Phenyl-4,5-dihydro-thiazolo[4,5-h]quinazoline-2,8-diamine.

In one preferred embodiment the compound of formula I is capable of exibiting an antiproliferative effect in human cell lines, as measured by a standard 72 h MTT cytotoxicity assay.

Preferably, the compound of formula I exihibits an $IC_{50}$ value of less than 10 µM.

Thus, in one particularly preferred embodiment of the invention, the compound of formula I is selected from the following:
(2-Methyl-4,5-dihydro-thiazolo[4,5-h]quinazolin-8-yl)-(3-nitro-phenyl)-amine;
(2-Methyl-4,5-dihydro-thiazolo[4,5-h]quinazolin-8-yl)-(4-trifluoromethyl-phenyl)-amine;
3-(2-Methyl-4,5-dihydro-thiazolo[4,5-h]quinazolin-8-ylamino)-phenol;
4-(2-Methyl-4,5-dihydro-thiazolo[4,5-h]quinazolin-8-ylamino)-phenol;
N,N-Dimethyl-N'-(2-methyl-4,5-dihydro-thiazolo[4,5-h]quinazolin-8-yl)-benzene-1,4-diamine;
(2-Methyl-4,5-dihydro-thiazolo[4,5-h]quinazolin-8-yl)-(4-morpholin-4-yl-phenyl)-amine;
(6-Methoxy-pyridin-3-yl)-(2-methyl-4,5-dihydro-thiazolo[4,5-h]quinazolin-8-yl)-amine; and
(6-Chloro-pyridin-3-yl)-(2-methyl-4,5-dihydro-thiazolo[4,5-h]quinazolin-8-yl)-amine.

More preferably, the compound of formula I exihibits an $IC_{50}$ value less than 5 µM, even more preferably less than 1 µM as measured by said MTT assay.

Thus, in one particularly preferred embodiment of the invention, the compound of formula I is (2-Methyl-4,5-dihydro-thiazolo[4,5-h]quinazolin-8-yl)-(3-nitro-phenyl)-amine.

Pharmaceutical Compositions

Another aspect of the invention relates to a pharmaceutical composition comprising a compound of formula 1 as defined above admixed with one or more pharmaceutically acceptable diluents, excipients or carriers. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of formula 1 can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of compounds of formula 1. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes the use of solvate forms of the compounds of the present invention. The terms used in the claims encompass these forms.

Polymorphs

The invention furthermore relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the compounds of the present invention in prodrug form. Such prodrugs are generally compounds of formula 1 wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules.

Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient.

Combinations

In a particularly preferred embodiment, one or more compounds of the invention are administered in combination with one or more other therapeutically active agents, for example, existing drugs available on the market. In such cases, the compounds of the invention may be administered consecutively, simultaneously or sequentially with the one or more other anticancer agents.

Anticancer drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Numerous combinations are used in current treatments of cancer and leukemia. A more extensive review of medical practices may be found in "Oncologic Therapies" edited by E. E. Vokes and H. M. Golomb, published by Springer.

Beneficial combinations may be suggested by studying the growth inhibitory activity of the test compounds with agents known or suspected of being valuable in the treatment of a particular cancer initially or cell lines derived from that cancer. This procedure can also be used to determine the order of administration of the agents, i.e. before, simultaneously, or after delivery. Such scheduling may be a feature of all the cycle acting agents identified herein.

Assays

Another aspect of the invention relates to the use of a compound of the invention as defined hereinabove in an assay for identifying further candidate compounds that influence the activity of one or more protein kinases.

Preferably, the assay is capable of identifying candidate compounds that are capable of inhibiting one or more of a CDK enzyme, aurora kinase, GSK or a PLK enzyme.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with a protein kinase in the presence of a known substrate of said protein kinase and detecting any change in the interaction between said protein kinase and said known substrate.

A further aspect of the invention provides a method of detecting the binding of a ligand to a kinase, said method comprising the steps of:

(i) contacting a ligand with a protein kinase in the presence of a known substrate of said protein kinase;

(ii) detecting any change in the interaction between said protein kinase and said known substrate;

and wherein said ligand is a compound of the invention.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;

(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of proliferative disorders.

The above methods may be used to screen for a ligand useful as an inhibitor of one or more protein kinases.

Synthesis

Compounds of general formula 1 can be prepared by any method known in the art. A convenient synthetic route is outlined below in Scheme 1:

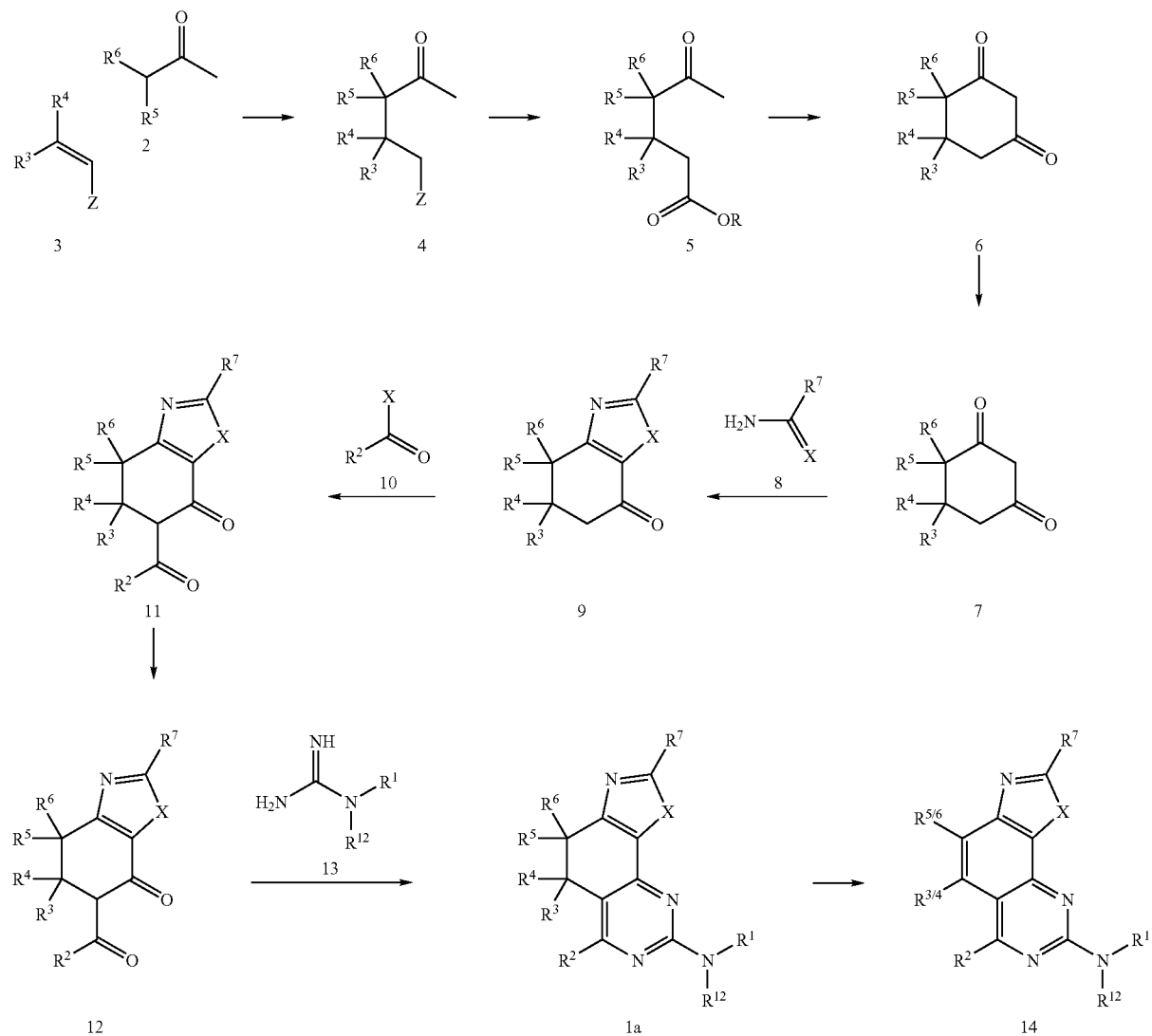

Michael reaction of enolisable—or preformed enolates derived from—methyl ketones 2 with activated alkenes 3 (where Z is an electron-withdrawing group such as CHO, COOR, CONH$_2$, CN, NO$_2$, SOR, SO$_2$R, etc.), affords ketones 4, whose Z group is converted to a carboxylic ester group (e.g. R=Me) in 1,5-dicarbonyl compounds 5. These are then cyclised under basic conditions to the cyclohexane-1,3-diones 6 [16-18]. Bromination yields the 2-bromo-cyclohexane-1,3-diones 7 [19,20], which are subsequently reacted with carboxamides (8, X=O), thioamides (8, X=S), or amidines (8, X=NH) to give 5,6-dihydro-4H-benzooxazol-7-ones (9, X=O), 5,6-dihydro-4H-benzothiazol-7-ones (9, R=S), and 3,5,6,7-tetrahydro-benzoimidazol-4-ones (9, R=NH), respectively. These compounds can then be acylated with carbonyl compounds 10 (where X is a leaving group such as Cl) to 1,3-dicarbonyl compounds 11; e.g. the formylation (R$^2$=H) of 5,6-dihydro-4H-benzothiazol-7-ones has been described in the literature [21]. Acyl derivatives 11 can be condensed directly with amidines [15] or guanidines 13. Alternatively, acyl derivatives 11 are first converted to enaminones 12 [22], from which 4,5-dihydro-oxazolo[4,5-h]quinazolin-8-ylamines (1, X=O), 4,5-dihydro-thiazolo[4,5-h]quinazolin-8-ylamines (1, X=S), and 4,5-dihydro-imidazolo[4,5-h]quinazolin-8-ylamines (1, X=NH) can be obtained. After guanylation, the aminopyridine N—H function can be acylated, alkylated or arylated depending on the nature of R$^1$ in 1. In the case where R$^1$ is an aryl group, Pd-catalyzed N-arylation of the heteroarylamine group can be achieved as described [63]. Fully aromatised analogues of 1, i.e. compounds of structure 14, can be obtained through oxidation.

A further aspect of the invention thus relates to a process for preparing compounds of formula 1, said process comprising the steps of:

(i) reacting a compound of formula 7 with a compound of formula 8 to form a compound of formula 9

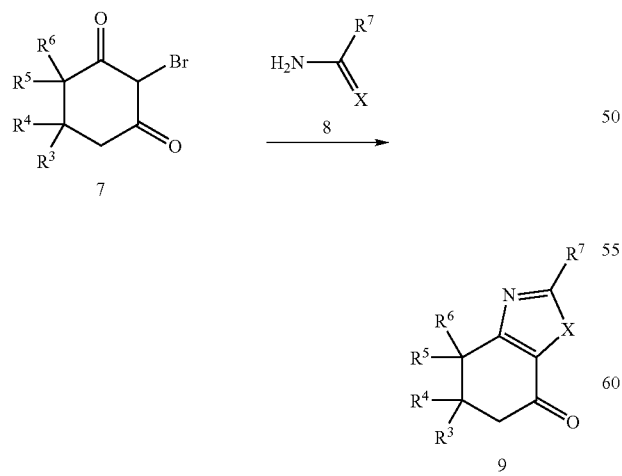

(ii) converting said compound of formula 9 into a compound of formula 1.

Preferably, the process further comprises the steps of:

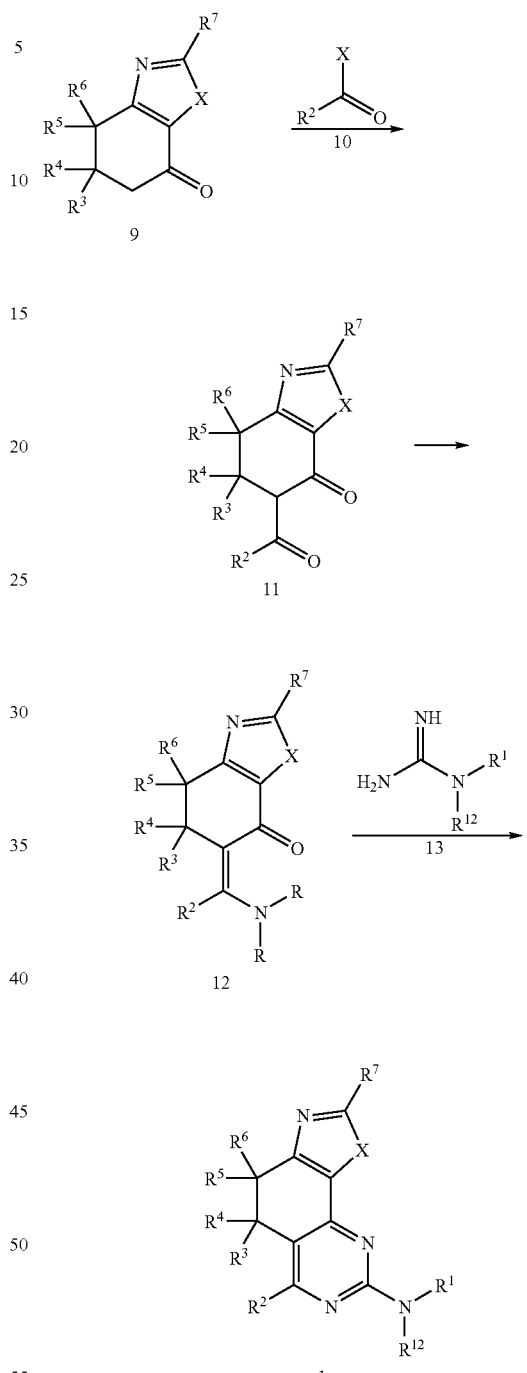

(i) reacting said compound of formula 9 with a compound of formula 10 to form a compound of formula 11;
(ii) converting said compound of formula 11 into a compound of formula 12;
(iii) reacting said compound of formula 12 with a compound of formula 13 to form a compound of formula 1a.

In one preferred embodiment, the process of the invention further comprises the steps of oxidising said compound of formula 1a to form a compound of formula 14.

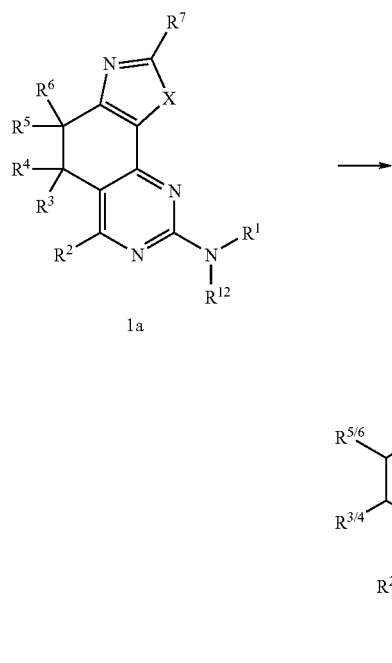

1a

14

The present invention is further illustrated by way of the following examples.

EXAMPLES

Abbreviations

NMR, nuclear magnetic resonance spectroscopy; r.t. room temperature; DMSO, dimethylsulfoxide.

Selected compounds of the invention are shown in Table 2.

General

Chemicals and solvents were purchased from commercial sources and were used as received unless otherwise stated. THF and $Et_2O$ were dried by heating under reflux with sodium-benzophenone under $N_2$ and collected by distillation. Toluene was dried by heating under reflux over sodium under $N_2$. $CH_2Cl_2$ was dried by heating under reflux over $CaH_2$ under $N_2$. The microwave generator used was a CEM "Discover" model, with a circular single mode cavity design, that focuses the microwave radiation on the sample tube. TLC (thin-layer chromatography) was performed using glass plates coated with silica gel G60 (0.25 cm). Developed plates were air dried and analysed under a UV lamp (254/365 nm). Anhydrous $MgSO_4$ was used as a standard drying agent for organic solutions unless otherwise stated. Flash column chromatography was performed using Fluorochem silica gel (35-70 μm). Melting points (mp) were determined with an Electrothermal 9100 capillary melting point apparatus and are uncorrected. The abbreviation (dec) denotes a decomposition point. $^1$H-NMR spectra were recorded on a Bruker Avance 300 (300.1 MHz) or a Varian Gemini 2000 (300 MHz) spectrometer using the deuterated solvent as the lock and the residual solvent as the internal reference in all cases. $^{13}$C-NMR spectra using the PENDANT sequence were recorded on a Bruker Avance 300 (75.5 MHz) spectrometer. All other $^{13}$C-spectra were recorded on a Varian Gemini 2000 (75.5 MHz) spectrometer using composite pulse $^1$H decoupling. Coupling constants (J) are quoted to the nearest 0.1 Hz. The following abbreviations are used: s, singlet; d, doublet; t, triplet; q, quartet; qu, quintuplet; m, multiplet and br, broad. Elemental microanalyses were performed by Mrs S Williamson, School of Chemistry, Purdie Building, University of St. Andrews, UK. Results obtained were within 0.4% of calculated values. Electrospray mass spectra (ESI) were recorded on a Micromass LCT mass spectrometer, coupled to a Waters 2975 HPLC. Analytical RP-HPLC was performed using a Dionex ASI-100 automated sample injector coupled to a Dionex P580 pump. A Phenomenex column (150×4.60 mm, Synergi 4 μ hydro-RP 80 Å), kept at a temperature of 25° C. Was used for analytical purposes. The HPLC unit was controlled using Chromeleon software. Linear gradient elution using $H_2O$/MeCN systems (containing 0.1% $CF_3COOH$) at flow rates of 1 mL/min was performed. Purity was assessed by integration of chromatograms (λ=254 nm).

2-Bromo-cyclohexane-1,3-dione

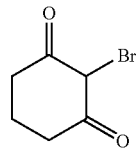

A solution of 1,3-cyclohexanedione (50 g, 0.45 mol) in $CH_2Cl_2$ (111 mL) was stirred at 5° C. Bromine (18 mL, 56.3 g, 0.35 mol) in $CH_2Cl_2$ (17 mL) was added dropwise over a period of 5-10 min. The reaction mixture was stirred at room temperature for 1 h. The brown precipitate that formed was collected by filtration, washed with $CH_2Cl_2$/toluene (100 mL), and air dried, before being crystallized from $H_2O$ to afford the title compound as pale yellow crystals (42.6 g, 50%): mp 167-168° C. Anal. RP-HPLC: $t_R$ 7.9 min (0-60% MeCN, purity 100%). $^1$H-NMR (DMSO-$d_6$): δ 2.49 (t, 4H, J 6.1, 2×$CH_2$), 1.85 (qu, 2H, J 6.1, $CH_2$). MS (ESI$^-$): m/z 190.90/188.90 (M-H)$^+$.

2-Methyl-5,6-dihydro-4H-benzothiazol-7-one

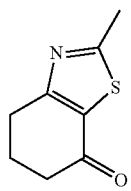

w To a solution of 2-bromo-cyclohexane-1,3-dione (20 g, 0.105 mol) in pyridine (150 mL) was added thioacetamide (7.9 g, 0.105 mol) and the mixture was stirred at 50° C. After 16 h the solvent was removed under vacuum. 10% aq NaCl solution (150 mL) was added and the product was extracted with $CH_2Cl_2$ (4×100 mL). The organic extracts were washed with additional 10% aq NaCl solution (2×100 mL) before being dried, filtered, and concentrated under vacuum. The dark viscous oil obtained was purified using a Kugelrohr distillation unit to afford the product as a yellow oil (6.97 g, 40%): $^1$H-NMR (CDCl$_3$): δ 3.02 (t, 2H, J 6.1, CH$_2$), 2.75 (s, 3H, CH$_3$), 2.61 (t, 2H, J 6.1, CH$_2$), 2.21 (qu, 2H, J 6.1, CH$_2$). $^{13}$C-NMR (CDCl$_3$): δ 192.1, 173.3, 166.8, 130.9, 37.8, 27.1, 23.1, 20.0. MS (ESI$^+$): m/z 168.03 (M+H)$^+$.

2-Amino-5,6-dihydro-4H-benzothiazol-7-one

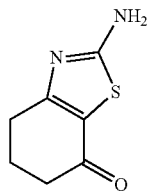

A solution of 2-bromo-cyclohexane-1,3-dione (1.0 g, 5.2 mmol) and thiourea (0.4 g, 5.2 mmol) in anhydrous EtOH (7 mL) was heated under reflux for 3 h. The reaction mixture was cooled, concentrated under vacuum, and washed with Et$_2$O (20 mL). The residue was dissolved in H$_2$O (10 mL) and 6 M aq NH$_4$OH (4 mL) was added dropwise. The yellow precipitate was collected, dried, and crystallised from EtOH to afford the titl compound as yellow crystals (0.41 g, 47%): mp 280-282° C. Anal. RP-HPLC: $t_R$ 7.2 min (0-60% MeCN, purity 100%). $^1$H-NMR (DMSO-d$_6$): δ 8.10 (s, 2H, NH$_2$), 2.65 (t, 2H, J 6.1, CH$_2$), 2.34 (t, 2H, J 6.1, CH$_2$), 1.97 (qu, 2H, J 6.1, CH$_2$). $^{13}$C NMR (DMSO-d$_6$): δ 189.8, 173.8, 168.5, 118.8, 37.1, 27.0, 22.8. MS: (ESI$^-$) m/z 166.99 (M–H)$^+$.

2-Methylamino-5,6-dihydro-4H-benzothiazol-7-one

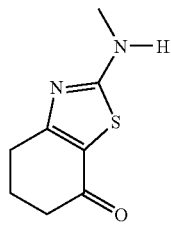

A solution of 2-bromo-cyclohexane-1,3-dione (8.0 g, 41.9 mmol) and methyl thiourea (3.77 g, 41.9 mmol) in pyridine (63 mL) was stirred at room temperature for 16 h. The reaction mixture was concentrated under vacuum, extracted with CH$_2$Cl$_2$/10% aq NaCl solution, dried, filtered, and concentrated under vacuum. Crystallization from EtOAc afforded the title compound as yellow crystals (3.26 g, 43%): mp 180-182° C. Anal. RP-HPLC: $t_R$ 8.4 min (0-60% MeCN, purity 100%). $^1$H-NMR (CDCl$_3$): δ 7.90 (s, 1H, NH), 2.99 (s, 3H, CH$_3$), 2.72 (t, 2H, J 6.1, CH$_2$), 2.49 (t, 2H, J 6.1, CH$_2$), 2.10 (qu, 2H, J 6.1, CH$_2$). $^{13}$C-NMR (CDCl$_3$): δ 191.0, 176.6, 168.0, 120.0, 37.5, 32.5, 27.7, 23.2. MS: (ESI$^+$) m/z 183.07 (M+H)$^+$.

2-Methyl-7-oxo-4, 5, 6, 7-tetrahydro-benzothiazole-6-carbaldehyde

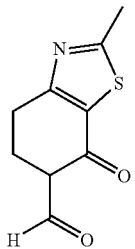

To a suspension of hexane-washed NaH (1.1 g, 44.8 mmol) in dry Et$_2$O (70 mL) was added dry MeOH (6.1 mL). After evolution of H$_2$ had subsided, freshly distilled ethyl formate (7.3 mL, 6.7 g, 89.7 mmol) was added, followed by 2-methyl-5,6-dihydro-4H-benzothiazol-7-one (3.0 g, 17.9 mmol) in dry Et$_2$O (12 mL). The reaction mixture was stirred at room temperature for 16 h. 10% aq HCl solution was added (150 mL) and the product was extracted with EtOAc (5×150 mL). The combined organic extracts were dried, filtered, and concentrated under vacuum to leave a brown oily crude product. Purification by flash column chromatography (20% EtOAc: hexane) afforded the pure title product as a yellow solid (2.30 g, 66%): mp 107-108° C. Anal. RP-HPLC: $t_R$ 12.6 min (0-60% MeCN, purity 100%). $^1$H-NMR (CDCl$_3$): δ 9.90 (s, CHO), 7.20 (s, 1H, CH), 2.91 (t, 2H, J 7.1, CH$_2$), 2.67 (s, 3H, CH$_3$), 2.58 (t, 2H, J 7.1, CH$_2$). $^{13}$C-NMR (CDCl$_3$): δ 198.6, 186.3, 174.2, 165.7, 162.6, 131.0, 108.4, 27.0, 24.5, 20.7. MS: (ESI$^-$) m/z 193.98 (M–H)$^+$.

2-Methyl-6-morpholin-4-ylmethylene-5,6-dihydro-4H-benzothiazol-7-one

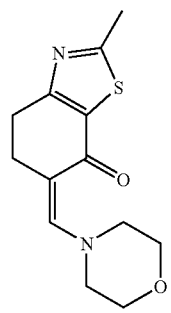

To a solution of 2-methyl-7-oxo-4,5,6,7-tetrahydro-benzothiazole-6-carbaldehyde (2.0 g, 10.2 mmol) in dry toluene (8.1 mL), morpholine (1.0 mL, 1.0 g, 11.3 mmol) was added. The reaction mixture was heated under reflux for 2 h. On cooling a brown precipitate formed. The solvent was removed under vacuum and the brown solid residue was fractionated by flash column chromatography (20% EtOAc:hexane) to leave a yellow solid that was purified further by crystallisation from EtOH to afford the pure title product as yellow crystals (2.4 g, 87%): mp 186-187° C. Anal. RP-HPLC: $t_R$ 12.7 min (0-60% MeCN, purity 100%). $^1$H-NMR (CDCl$_3$): δ 7.50 (s, 1H, CH), 3.80 (t, 4H, J 4.6), 3.55 (t, 4H, J 4.6), 3.00 (m, 4H, CH$_2$—CH$_2$), 2.80 (s, 3H, CH$_3$). $^{13}$C-NMR (CDCl$_3$): δ 182.0, 171.6, 162.3, 147.9, 133.2, 103.3, 67.0, 51.4, 26.7, 24.9, 20.2. MS (ESI+): m/z 287.05 (M+Na)+, 265.07 (M+H)+. Anal. ($C_{13}H_{16}N_2O_2S$)C, H, N.

(2-Methyl-4,5-dihydro-thiazolo[4,5-h]quinazolin-8-yl)-(3-nitro-phenyl)-amine

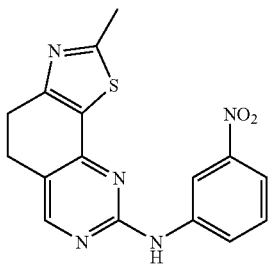

A mixture of 2-methyl-7-oxo-4,5,6,7-tetrahydro-benzothiazole-6-carbaldehyde (200 mg, 1 mmol), meta-nitrophenyl guanidine nitrate (248 mg, 1), NaOH (41 mg, 1 mmol) and 2-methoxyethanol (2 mL) was heated under reflux for 16 h. The reaction mixture was concentrated under vacuum. Flash column chromatography (20% EtOAc:hexane) gave the title compound as a yellow solid (18 mg, 5%): mp 227-228° C. Anal. RP-HPLC: $t_R$ 21.9 min (0-60% MeCN, purity 100%). $^1$H-NMR (DMSO-$d_6$): δ 10.00 (s, 1H, NH), 8.89 (t, 1H, J 2.3, Ph-H), 8.30 (s, 1H, Py-H), 7.92 (ddd, 1H, J 8.3, 2.3, 0.7, Ph-H), 7.66 (ddd, 1H, J 8.3, 2.3, 0.7, Ph-H), 7.44 (t, 1H, J 8.3, Ph-H), 2.90 (m, 4H, $CH_2$—$CH_2$), 2.66 (s, 3H, $CH_3$). $^{13}$C-NMR (DMSO-$d_6$): δ 169.16, 159.27, 158.42, 156.05, 155.39, 148.04, 142.02, 129.57, 127.56, 124.22, 117.13, 115.16, 111.91, 24.56, 23.06, 19.48. MS (ESI−): m/z 337.94 (M−H)+.

(2-Methyl-4,5-dihydro-thiazolo[4,5-h]quinazolin-8-yl)-(4-trifluoromethyl-phenyl)-amine

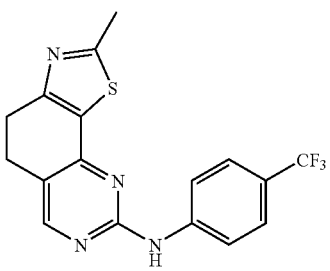

A mixture of 2-methyl-7-oxo-4,5,6,7-tetrahydro-benzothiazole-6-carbaldehyde (200 mg, 1.02 mmol), N-(4-trifluoromethyl-phenyl)-guanidine nitrate (273 mg, 1.02 mmol), NaOH (41 mg, 1.02 mmol) and 2-methoxyethanol (1.25 mL) was heated under reflux for 16 h. The reaction mixture was concentrated under vacuum. Flash column chromatography (20% EtOAc:hexane) followed by crystallisation from EtOAc gave the pure title compound as a white crystalline solid (30 mg, 8%): mp 212-213° C. Anal. RP-HPLC: $t_R$ 21.8 min (10-70% MeCN, purity 95%). $^1$H-NMR (CDCl$_3$): δ 8.17 (s, 1H, Py-H), 7.71 (d, 2H, J 8.4, Ph-H), 7.52 (d, 2H, J 8.4, Ph-H), 7.16 (s, 1H, NH), 3.04 (t, 2H, J 6.6, $CH_2$), 2.94 (t, 2H, J 6.6, $CH_2$), 2.72 (s, 3H, $CH_3$). MS (ESI−): m/z 360.95 (M−H)+.

3-(2-Methyl-4,5-dihydro-thiazolo[4,5-h]quinazolin-8-ylamino)-phenol

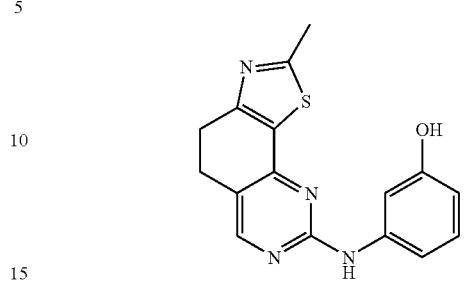

A mixture of 2-methyl-6-morpholin-4-ylmethylene-5,6-dihydro-4H-benzothiazol-7-one (210 mg, 7.94 mmol), N-(3-hydroxy-phenyl)-guanidine nitrate (170 mg, 7.94 mmol), NaOH (32 mg, 7.94 mmol), and 2-methoxyethanol (2 mL) was heated under reflux for 16 h. The reaction mixture was concentrated under vacuum. Flash column chromatography (10% MeOH:EtOAc) gave the pure title product as a yellow solid (20 mg, 8%): mp 310° C. (dec). Anal. RP-HPLC: $t_R$ 10.3 min (0-60% MeCN, purity 92%). $^1$H-NMR (DMSO-$d_6$): δ 9.50 (s, 1H, OH/NH), 9.28 (s, 1H, OH/NH), 8.38 (s, 1H, Py-H), 7.37 (t, 1H, J 2.3, Ph-H), 7.27 (ddd, 1H, J 8.3, 2.3, 0.7, Ph-H), 7.08 (t, 1H, J 8.3, Ph-H), 6.40 (ddd, 1H, J 8.3, 2.3, 0.7, Ph-H), 3.05 (m, 4H, $CH_2$—$CH_2$), 2.78 (s, 3H, $CH_3$). $^{13}$C-NMR (DMSO-$d_6$): δ 168.71, 159.05, 158.88, 157.42, 155.97, 155.20, 141.75, 128.81, 127.83, 115.89, 109.69, 108.35, 105.87, 24.72, 23.09, 19.38. MS (ESI+): m/z 311.06 (M+H)+.

(2-Methyl-4,5-dihydro-thiazolo[4,5-h]quinazolin-8-yl)-(4-morpholin-4-yl-phenyl)-amine

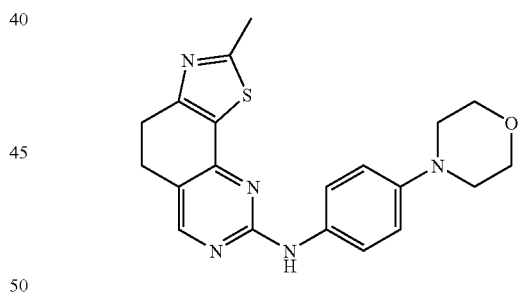

A mixture of 2-methyl-6-morpholin-4-ylmethylene-5,6-dihydro-4H-benzothiazol-7-one (200 mg, 7.6 mmol), N-(4-morpholin-4-yl-phenyl)-guanidine nitrate (215 mg, 7.6 mmol), NaOH (30 mg, 7.6 mmol), and 2-methoxyethanol (2 mL) was heated under reflux for 20 h. The reaction mixture was concentrated under vacuum. Flash column chromatography (5% MeOH:$CH_2Cl_2$), followed by crystallisation from EtOAc gave the pure title product as dark orange crystals (60 mg, 21%): mp 236-237° C. Anal. RP-HPLC: $t_R$ 13.4 min (0-60% MeCN, purity 100%). $^1$H-NMR (DMSO-$d_6$): δ 9.26 (s, 1H, NH), 8.20 (s, 1H, Py-H), 7.58 (d, 2H, J 9.2, Ph-H), 6.84 (d, 2H, J 9.2, Ph-H), 3.70 (t, 4H, J 4.8, 2×$CH_2$), 2.99 (t, 4H, J 4.8, 2×$CH_2$), 2.90 (m, 4H, $CH_2$—$CH_2$), 2.66 (s, 3H, $CH_3$).

$^{13}$C-NMR (DMSO-$d_6$): δ 168.99, 159.53, 159.19, 155.75, 146.24, 133.60, 120.14, 115.97, 115.61, 66.52, 49.67, 25.12, 23.45, 19.80. MS (ESI+): m/z 380.10 (M+H)+.

27

4-(2-Methyl-4,5-dihydro-thiazolo[4,5-h]quinazolin-8-ylamino)-phenol

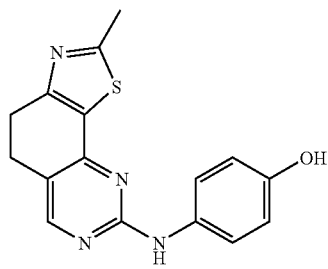

A mixture of 2-methyl-6-morpholin-4-ylmethylene-5,6-dihydro-4H-benzothiazol-7-one (200 mg, 7.6 mmol), N-(4-hydroxy-phenyl)-guanidine nitrate (163 mg, 7.6 mmol), NaOH, (30 mg, 7.6 mmol), and 2-methoxyethanol (2 mL) was heated at 120° C. for 24 h. The reaction mixture was concentrated under vacuum. Flash column chromatography (20% EtOAc:hexane) gave the title product as a yellow solid (70 mg, 30%): mp 268-269° C. Anal. RP-HPLC: $t_R$ 12.4 min (10-70% MeCN, purity 95%). $^1$H-NMR (DMSO-$d_6$): δ 9.28 (s, 1H, OH/NH), 9.07 (s, 1H, OH/NH), 8.30 (s, 1H, Py-H), 7.58 (d, 2H, J 8.9, Ph-H), 6.75 (d, 2H, J 8.9, Ph-H), 3.02 (m, 4H, CH$_2$—CH$_2$), 2.80 (s, 3H, CH$_3$). $^{13}$C-NMR (DMSO-$d_6$): δ 168.94, 159.64, 159.13, 156.26, 155.73, 152.35, 132.70, 120.94, 115.44, 115.19, 25.13, 23.45, 19.79. MS (ESI$^+$): m/z 311.06 (M+H)$^+$.

N,N-Dimethyl-N'-(2-methyl-4,5-dihydro-thiazolo[4,5-h]quinazolin-8-yl)-benzene-1,4-diamine

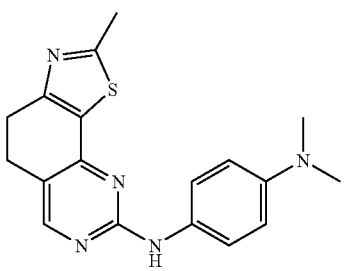

A mixture of 2-methyl-6-morpholin-4-ylmethylene-5,6-dihydro-4H-benzothiazol-7-one (119 mg, 4.5 mmol), N-(4-dimethylamino-phenyl)-guanidine nitrate (137 mg, 4.5 mmol), NaOH (18 mg, 4.5 mmol), and 2-methoxyethanol (2 mL) was heated at 100° C. for 5 h. The reaction mixture was concentrated under vacuum. Flash column chromatography (20% EtOAc:hexane) gave the title product as a dark yellow solid (140 mg, 92%): mp 176-177° C. Anal. RP-HPLC: $t_R$ 11.9 min (0-60% MeCN, purity 100%). $^1$H-NMR (DMSO-$d_6$): δ 9.23 (s, 1H, NH), 8.28 (s, 1H, Py-H), 7.60 (d, 2H, J 9.2, Ph-H), 6.75 (d, 2H, J 9.2, Ph-H), 3.02 (m, 4H, CH$_2$—CH$_2$), 2.88 (s, 6H, NMe$_2$), 2.75 (s, 3H, CH$_3$). $^{13}$C-NMR (DMSO-$d_6$): δ 168.90, 159.67, 159.08, 155.77, 146.32, 131.16, 120.65, 115.25, 113.32, 41.14, 25.15, 23.45, 19.79. MS (ESI$^+$): m/z 338.10 (M+H)$^+$.

28

(6-Chloro-pyridin-3-yl)-(2-methyl-4,5-dihydro-thiazolo[4,5-h]quinazolin-8-yl)-amine

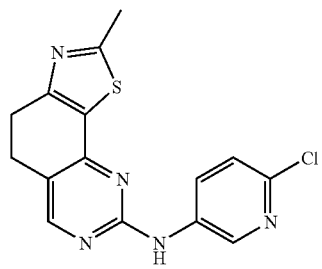

A mixture of 2-methyl-6-morpholin-4-ylmethylene-5,6-dihydro-4H-benzothiazol-7-one (200 mg, 0.76 mmol), N-(6-chloro-pyridin-3-yl)-guanidine nitrate (196 mg, 0.84 mmol), NaOH (34 mg, 0.84 mmol) and 2-methoxyethanol (2 mL) was heated at 100° C. for 24 h. The reaction mixture was concentrated under vacuum. Flash column chromatography (20% EtOAc:hexane) gave the pure title product as a white solid (40 mg, 16%): mp 252-253° C. Anal. RP-HPLC: $t_R$ 16.8 min (10-70% MeCN, purity 92%). $^1$H-NMR (DMSO-$d_6$) δ 9.98 (s, 1H, NH), 8.90 (d, 1H, J 2.9, Ph-H), 8.44 (s, 1H, Py-H), 8.29 (dd, 1H, J 8.7, 2.4, Ph-H), 7.50 (d, 1H, J 8.7, Ph-H), 3.10 (m, 4H, CH$_2$—CH$_2$), 2.82 (s, 3H, CH$_3$). $^{13}$C-NMR (DMSO-$d_6$): δ 169.08, 159.26, 158.47, 156.22, 155.35, 141.23, 139.69, 137.05, 128.55, 127.52, 123.55, 117.05, 24.60, 23.07, 19.39. MS (ESI$^+$): m/z 330.06 (M+H)$^+$.

(6-Methoxy-pyridin-3-yl)-(2-methyl-4,5-dihydro-thiazolo[4,5-h]quinazolin-8-yl)-amine

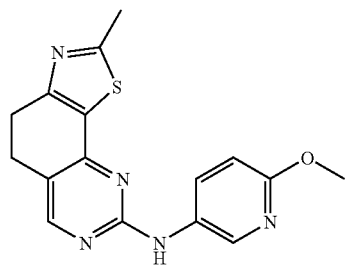

A mixture of 2-methyl-6-morpholin-4-ylmethylene-5,6-dihydro-4H-benzothiazol-7-one (200 mg, 0.76 mmol), N-(6-methoxy-pyridin-3-yl)-guanidine nitrate (192 mg, 0.84 mmol), NaOH (34 mg, 0.84 mmol) and 2-methoxyethanol (2 mL) was heated at 100° C. for 24 h. The reaction mixture was concentrated under vacuum. Flash column chromatography (20% EtOAc:hexane) gave the title product as a white solid (20 mg, 8%): mp 210-211° C. Anal. RP-HPLC: $t_R$ 11.6 min (10-70% MeCN, purity 93%). $^1$H-NMR (CDCl$_3$): δ 8.42 (d, 1H, J 2.4, Ph-H), 8.26 (s, 1H, Py-H), 8.08 (dd, 1H, J 9.1, 2.9, Ph-H), 7.19 (brs, 1H, NH), 6.86 (d, 1H, J 9.1, Ph-H), 4.04 (s, 3H, OMe), 3.13 (m, 4H, CH$_2$—CH$_2$), 2.87 (s, 3H, CH$_3$). $^{13}$C-NMR (CDCl$_3$): δ 169.47, 159.97, 159.38, 159.12, 157.10, 155.16, 137.95, 131.90, 130.45, 128.62, 116.48, 110.33, 53.49, 25.29, 23.92, 19.84. MS (ESI$^+$): m/z 326.08 (M+H)$^+$.

Methyl-(2-methyl-4,5-dihydro-thiazolo[4,5-h]quinazolin-8-yl)-(3-nitro-phenyl)-amine

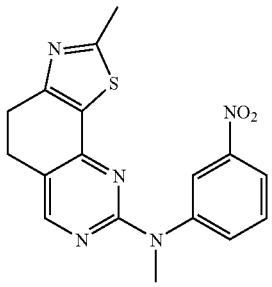

To a solution of (2-methyl-4,5-dihydro-thiazolo[4,5-h]quinazolin-8-yl)-(3-nitro-phenyl)-amine (100 mg, 0.3 mmol) in dry DMF (2 mL) was added NaH (7.8 mg, 0.3 mmol) under anhydrous conditions. Once H$_2$ evolution had ceased, iodomethane (22 μL, 50 mg, 0.4 mmol) was added dropwise and the mixture was stirred at room temperature overnight. It was then concentrated under vacuum and H$_2$O (20 mL) was added. The product was extracted with CH$_2$Cl$_2$ (3×30 mL). The combined extracts were dried, filtered, and concentrated under vacuum. Flash column chromatography (10% EtOAc:hexane) afforded the pure title product as a yellow solid (40 mg, 38%): mp 203-204° C. Anal. RP-HPLC: t$_R$ 17.1 min (10-70% MeCN, purity 85%). $^1$H-NMR (CDCl$_3$): δ 8.30 (t, 1H, J 2.3, Ph-H), 8.11 (s, 1H, Py-H), 7.95 (ddd, 1H, J 8.2, 2.3, 1.0, Ph-H), 7.65 (ddd, 1H, J 8.2, 2.3, 1.0, Ph-H), 7.44 (t, 1H, J 8.2, Ph-H), 3.58 (s, 3H, N—CH$_3$), 2.98 (m, 4H, CH$_2$—CH$_2$), 2.69 (s, 3H, CH$_3$). $^{13}$C-NMR (CDCl$_3$): δ 169.86, 160.70, 159.30, 157.05, 155.27, 148.71, 146.74, 131.42, 129.33, 120.81, 119.36, 116.63, 38.18, 25.68, 24.22, 20.17. MS (ESI$^+$): m/z 354.09 (M+H)$^+$.

Methyl-(2-methyl-thiazolo[4,5-h]quinazolin-8-yl)-(3-nitro-phenyl)-amine

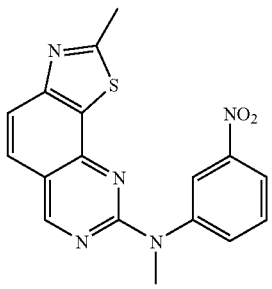

Under dry conditions, a mixture of methyl-(2-methyl-4,5-dihydro-thiazolo[4,5-h]quinazolin-8-yl)-(3-nitro-phenyl)-amine (16 mg, 0.045 mmol) and 2,3-dichloro-5,6-dicyano-1,4-benzoquinone (DDQ) (10.2 mg, 0.045 mmol) in dry toluene (2 mL) was heated under reflux for 16 h. The solvent was evaporated under vacuum and the residue was purified by flash column chromatography (10% EtOAc:hexane) to afford the title product as a yellow solid (10 mg, 68%). mp 209-210° C. Anal. RP-HPLC: t$_R$ 23.4 min (10-70% MeCN, purity 98%). $^1$H-NMR (CDCl$_3$): δ 9.09 (s, 1H, Py-H), 8.41 (t, 1H, J 2.3, Ph-H), 8.09 (ddd, 1H, J 8.2, 2.3, 1.0, Ph-H), 7.85 (d, 1H, J 8.7, Ph-H), 7.79 (ddd, 1H, J 8.2, 2.3, 1.0, Ph-H), 7.72 (d, 1H, J 8.7, Ph-H), 7.58 (t, 1H, J 8.2, Ph-H), 3.78 (s, 3H, N—CH$_3$), 2.94 (s, 3H, Me). $^{13}$C-NMR (CDCl$_3$): δ 171.04, 161.09, 158.53, 157.16, 148.54, 148.04, 146.25, 131.74, 129.31, 125.29, 121.01, 119.85, 119.30, 116.97, 38.39, 20.48 missing 1 quat signal. MS (ESI$^+$): m/z 352.08 (M+H)$^+$.

(2-Methyl-4,5-dihydro-thiazolo[4,5-h]quinazolin-8-yl)-phenyl-amine

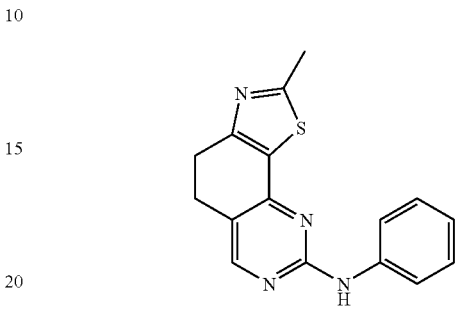

A mixture of 2-methyl-6-morpholin-4-ylmethylene-5,6-dihydro-4H-benzothiazol-7-one (300 mg, 1.1 mmol), N-phenyl-guanidine nitrate (449 mg, 2.3 mmol), NaOH (109 mg, 2.7 mmol) and 2-methoxyethanol (5 mL) was heated at 100° C. for 8 h. The reaction mixture was concentrated under vacuum. Flash column chromatography (20% EtOAc hexane) followed by crystallisation from EtOH afforded the title product as a white solid (154 mg, 46%): mp 223-224° C. Anal. RP-HPLC: t$_R$ 17.1 min (0-60% MeCN, purity 100%). $^1$H-NMR (CDCl$_3$): δ 8.19 (s, 1H, Py-H), 7.64 (d, 2H, J 7.4, Ph-H), 7.33 (t, 2H, J 7.4, Ph-H), 7.27 (brs, 1H, NH), 7.02 (t, 1H, J 7.4, Ph-H), 3.02 (m, 4H, CH$_2$—CH$_2$), 2.76 (s, 3H, CH$_3$). $^{13}$C-NMR (CDCl$_3$): δ 169.47, 159.20, 159.10, 157.05, 155.22, 139.82, 128.96, 128.84, 122.22, 118.89, 116.57, 25.38, 24.03, 19.93. MS (ESI$^+$): m/z 295.08 (M+H)$^+$.

(2-Methyl-thiazolo[4,5-h]quinazolin-8-yl)-phenyl-amine

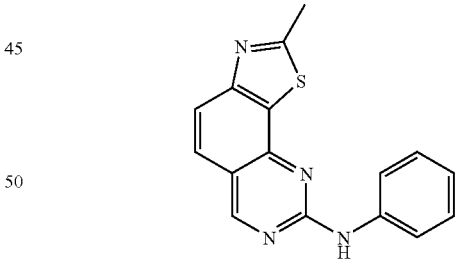

(2-Methyl-4,5-dihydro-thiazolo[4,5-h]quinazolin-8-yl)-phenyl-amine (52 mg, 0.18 mmol) and DDQ (48 mg, 0.21 mmol) in toluene (10 mL) were heated under reflux for 16 h using anhydrous conditions. The reaction mixture was diluted with EtOAc, filtered, and concentrated under vacuum. Purification of the residue by flash column chromatography (20% EtOAc:hexane) afforded the title product as a yellow solid (22 mg, 43%): mp 216° C. (dec). Anal. RP-HPLC: t$_R$ 15.1 min (0-60% MeCN, purity 100%). $^1$H-NMR (DMSO-d$_6$): δ 10.11 (s, 1H, NH), 9.38 (s, 1H, Py-H), 7.98 (d, 2H, J 7.7, Ph-H), 7.93 (d, 1H, J 8.7, CH), 7.84 (d, 1H, J 8.7, CH), 7.36 (t, 2H, J 7.7, Ph-H), 7.02 (t, 1H, J 7.7, Ph-H), 2.91 (s, 3H, CH$_3$). MS (ESI$^+$): m/z 293.07 (M+H)$^+$.

N'-(6-Dimethylaminomethylene-7-oxo-4, 5,6,7-tetrahydro-benzothiazol-2-yl)-N,N-dimethyl-formamidine

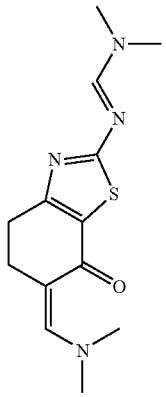

A mixture of 2-amino-5,6-dihydro-4H-benzothiazol-7-one (0.5 g, 3 mmol) and N,N-dimethylformamide dimethyl acetal (1.96 mL, 1.76 g, 14.8 mmol) in EtOH (2 mL) was heated under microwave irradiation (300 W, 150° C.) for 30 min. The mixture was concentrated under vacuum before purification by flash column chromatography (50% EtOAc:hexane) to afford the title product as a tan solid (0.49 g, 59%): mp 185-186° C. Anal. RP-HPLC: $t_R$ 9.3 min (0-60% MeCN, purity 100%). $^1$H-NMR (CDCl$_3$): δ 8.23 (s, 1H, CH), 7.44 (s, 1H, CH), 3.13 (s, 3H, CH$_3$), 3.11 (s, 3H, CH$_3$), 3.08 (s, 6H, N(CH$_3$)$_2$), 3.00 (t, 2H, J 6.6, CH$_2$), 2.83 (t, 2H, J 6.6, CH$_2$). MS (ESI$^+$): m/z 279.15 (M+H)$^+$.

N$^8$-Phenyl-4,5-dihydro-thiazolo[4,5-h]quinazoline-2,8-diamine

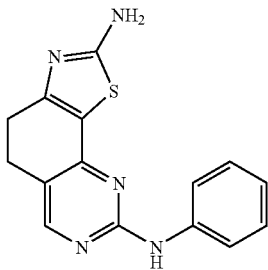

A mixture of N'-(6-dimethylaminomethylene-7-oxo-4,5,6,7-tetrahydro-benzothiazol-2-yl)-N,N-dimethyl-formamidine (200 mg, 0.72 mmol), N-phenyl-guanidine nitrate (142 mg, 0.72 mmol), NaOH (57 mg, 1.44 mmol) and 2-methoxyethanol (4 mL) was heated under microwave irradiation (300 W, 100° C.) for 30 min. The reaction mixture was concentrated under vacuum. Flash column chromatography (20% EtOAc:hexane) afforded the title product as a dark yellow solid (16 mg, 8%): mp 240° C. (dec). $^1$H-NMR (DMSO-d$_6$): δ 9.42 (s, 1H, NH), 8.23 (s, 1H, Py-H), 7.77 (d, 2H, J 7.7, Ph-H), 7.26 (t, 2H, J 7.7, Ph-H), 6.91 (t, 1H, J 7.2, Ph-H), 2.93 (s, 4H, CH$_2$—CH$_2$). MS (ESI$^+$): m/z 296.07 (M+H)$^+$.

N$^8$-(3-Nitro-phenyl)-4,5-dihydro-thiazolo[4,5-h]quinazoline-2,8-diamine

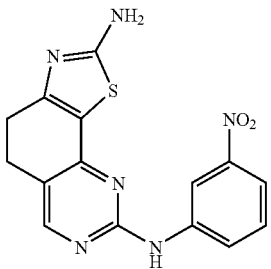

A mixture of N'-(6-dimethylaminomethylene-7-oxo-4,5,6,7-tetrahydro-benzothiazol-2-yl)-N,N-dimethyl-formamidine (188 mg, 0.68 mmol), meta-nitro-phenyl guanidine nitrate (328 mg, 1.35 mmol), NaOH (54 mg, 1.35 mmol) and 2-methoxyethanol (5 mL) was heated under reflux for 24 h. The reaction mixture was concentrated under vacuum. Flash column chromatography (20% EtOAc:hexane) afforded the pure product as a dark yellow solid (25 mg, 11%): mp 320° C. (dec). Anal. RP-HPLC: $t_R$ 14.7 min (0-60% MeCN, purity 100%). $^1$H-NMR (DMSO-d$_6$): δ 9.86 (s, 1H, NH), 8.99 (t, 1H, J 2.3, Ph-H), 8.14 (s, 1H, Py-H), 8.00 (ddd, 1H, J 8.2, 2.3, 0.7, Ph-H), 7.86 (brs, 2H, NH$_2$), 7.73 (ddd, 1H, J 8.2, 2.3, 0.7, Ph-H), 7.51 (t, 1H, J 8.2, Ph-H), 2.82 (m, 4H, CH$_2$—CH$_2$).
$^{13}$C-NMR (DMSO-d$_6$): δ 171.80, 159.94, 158.36, 157.39, 152.89, 148.11, 142.40, 129.49, 124.08, 115.88, 114.81, 114.59, 111.77, 25.22, 23.02. MS (ESI$^+$): m/z 340.94 (M+H)$^+$.

2-Methyl-4,5-dihydro-thiazolo[4,5-h]quinazolin-8-ylamine

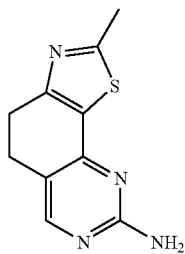

A mixture of 2-methyl-6-morpholin-4-ylmethylene-5,6-dihydro-4H-benzothiazol-7-one (2.24 g, 8.47 mol), guanidine hydrochloride salt (0.89 g, 9.32 mol) and NaOH (0.37 g, 9.32 mol) in EtOH (150 mL) was heated under reflux for 4 h. The reaction mixture was concentrated under vacuum. Flash column chromatography (50% EtOAc:hexane) afforded the title product as a yellow solid (1.66 g, 90%): mp 241-243° C. Anal. RP-HPLC: $t_R$ 8.7 min (0-60% MeCN, purity 100%). $^1$H-NMR (CDCl$_3$): δ 8.06 (s, 1H, Py-H), 5.01 (brs, 2H, NH$_2$), 2.99 (m, 4H, CH$_2$—CH$_2$), 2.76 (s, 3H, CH$_3$). MS (ESI$^+$): m/z 219.02 (M+H)$^+$.

N-(2-Methyl-4,5-dihydro-thiazolo[4,5-h]quinazolin-8-yl)-benzamide

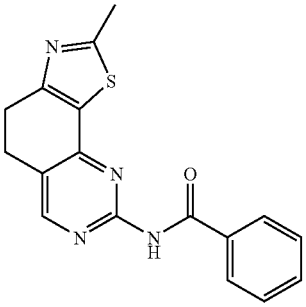

To 2-methyl-4,5-dihydro-thiazolo[4,5-h]quinazolin-8-ylamine (0.2 g, 0.92 mmol) in pyridine (7 mL) was added benzoyl chloride (117 μL, 142 mg, 1 mmol). The mixture was stirred at room temperature for 2 h. Water (100 mL) was added and the product was extracted into EtOAc (3×50 mL). The organic extracts were combined, dried, filtered, and concentrated under vacuum. Flash column chromatography (50% EtOAc:hexane) followed by crystallisation from EtOH afforded the title product as yellow crystals (173 mg, 59%): mp 229-231° C. Anal. RP-HPLC: $t_R$ 13.5 min (0-60% MeCN, purity 100%). $^1$H-NMR (CDCl$_3$): δ 8.59 (s, 1H, NH), 8.44 (s, 1H, Py-H), 7.95 (m, 2H, Ph-H), 7.54 (m, 3H, Ph-H), 3.09 (m, 4H, CH$_2$—CH$_2$), 2.77 (s, 3H, CH$_3$). $^{13}$C-NMR (CDCl$_3$): δ 170.70, 165.50, 160.05, 158.04, 157.02, 155.77, 134.89, 132.66, 129.15, 128.92, 127.89, 121.44, 25.39, 24.50, 20.31. MS (ESI$^+$): m/z 323.05 (M+H)$^+$. Anal. (C$_{17}$H$_{14}$N$_4$OS)C, H, N.

Benzyl-(2-methyl-4,5-dihydro-thiazolo[4,5-h]quinazolin-8-yl)-amine

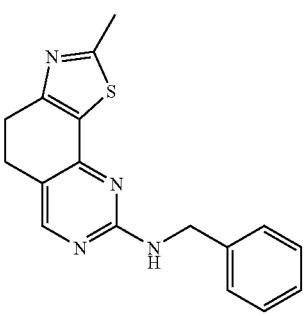

To 2-methyl-4,5-dihydro-thiazolo[4,5-h]quinazolin-8-ylamine (100 mg, 0.46 mmol) in dry THF (10 mL), cooled to −78° C., was added LiHMDS (458 μL, 0.46 mmol). The mixture was stirred for 15 min before benzyl bromide (65 μL, 94 mg, 0.55 mmol) was added. The solution was stirred at −78° C. and allowed to warm to room temperature over a period of 16 h. Ammonium chloride solution was added (100 mL) and the product was extracted with CH$_2$Cl$_2$ (3×50 mL). The organic extracts were combined, dried, filtered, and concentrated under vacuum. Flash column chromatography (20% EtOAc:hexane) followed by crystallisation from EtOH gave the title product as orange crystals (28 mg, 20%): mp 152-154° C. $^1$H-NMR (CDCl$_3$): δ 8.07 (s, 1H, Py-H), 7.40-7.25 (m, 5H, Ph-H), 5.47 (brs, 1H, NH), 4.64 (d, 2H, J 5.8, CH$_2$), 2.98 (m, 4H, CH$_2$—CH$_2$), 2.75 (s, 3H, CH$_3$). MS (ESI$^+$): m/z 309.11 (M+H)$^+$. Anal. (C$_{17}$H$_{16}$N$_4$S)C, H, N.

(2-Methyl-4,5-dihydro-thiazolo[4,5-h]quinazolin-8-yl)-carbamic acid but-3-enyl ester

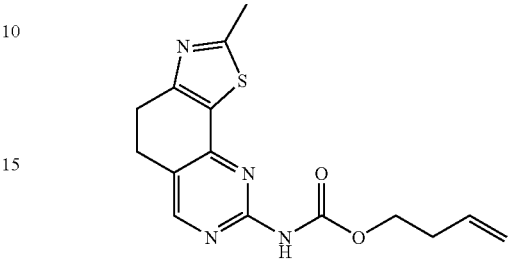

To 2-methyl-4,5-dihydro-thiazolo[4,5-h]quinazolin-8-ylamine (100 mg, 0.46 mmol) in pyridine (3 mL) was added 3-butenyl chloroformate (68 μL, 74 mg, 0.55 mmol). The mixture was stirred at room temperature for 16 h. Ammonium chloride solution was added (50 mL) and the product was extracted with CH$_2$Cl$_2$ (3×50 mL). The organic extracts were combined, dried, filtered, and concentrated under vacuum to give a yellow solid. Crystallisation from EtOAc afforded the pure title product as yellow crystals (122 mg, 84%): mp 204° C. (dec). Anal. RP-HPLC: $t_R$ 14.1 min (0-60% MeCN, purity 100%). $^1$H-NMR (CDCl$_3$): δ 8.36 (s, 1H, Py-H), 7.49 (brs, 1H, NH), 5.90-5.75 (m, 1H, CH), 5.19-5.07 (m, 2H, CH$_2$), 4.27 (t, 2H, J 6.6, CH$_2$), 3.06 (m, 4H, CH$_2$—CH$_2$), 2.77 (s, 3H, CH$_3$), 2.45 (m, 2H, CH$_2$). MS (ESI$^+$): m/z 339.00 (M+Na)$^+$.

N-(2-Methyl-4,5-dihydro-thiazolo[4,5-h]quinazolin-8-yl)-benzenesulfonamide

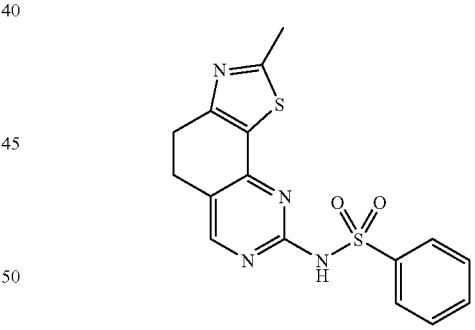

Under anhydrous conditions pyridine (5 mL) was added to 2-methyl-4,5-dihydro-thiazolo[4,5-h]quinazolin-8-ylamine (148 mg, 0.68 mmol). The mixture was stirred at 60° C. for 1 h before benzenesulfonyl chloride (121 μL, 168 mg, 0.95 mmol) was added. After 16 h the mixture was cooled and evaporated to dryness. Flash column chromatography (20% EtOAc:hexane) gave the title product as a tan solid (86 mg, 35%): mp 265° C. (dec). Anal. RP-HPLC: $t_R$ 15.5 min (0-60% MeCN, purity 100%). $^1$H-NMR (DMSO-d$_6$): δ 8.25 (s, 1H, Py-H), 8.03-7.98 (m, 2H, Ph-H), 7.62-7.55 (m, 3H, Ph-H), 2.92 (m, 4H, CH$_2$—CH$_2$), 2.73 (s, 3H, CH$_3$). $^{13}$C-NMR (DMSO-d$_6$): δ 170.15, 160.04, 156.92, 155.66, 153.95, 140.76, 132.51, 128.60, 127.70, 126.97, 118.96, 24.35, 22.94, 19.51. MS (ESI$^+$): m/z 380.97 (M+Na)$^+$.

Biological Activity

Compounds were tested in cyclin-CDK kinase assays and cytotoxicity assays against human tumour cell lines (72-h MTT assay) as previously described [9]. The results are summarised in Table 1 below.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

REFERENCES

1. Manning, G.; Whyte, D. B.; Martinez, R.; Hunter, T.; Sudarsanam, S. The protein kinase complement of the human genome. *Science* 2002, 298, 1912-1934.
2. Kostich, M.; English, J.; Madison, V.; Gheyas, F.; Wang, L. et al. Human members of the eukaryotic protein kinase family. *Genome Biology* 2002, 3, research0043.0041-0043.0012.
3. Dancey, J.; Sausville, E. A. Issues and progress with protein kinase inhibitors for cancer treatment. *Nat. Rev. Drug Disc.* 2003, 2, 296-313.
4. Cockerill, G. S.; Lackey, K. E. Small molecule inhibitors of the class 1 receptor tyrosine kinase family. *Current Topics in Medicinal Chemistry* 2002, 2, 1001-1010.
5. Fabbro, D.; Ruetz, S.; Buchdunger, E.; Cowan-Jacob, S. W.; Fendrich, G. et al. Protein kinases as targets for anticancer agents: from inhibitors to useful drugs. *Pharmacol. Ther.* 2002, 93, 79-98.
6. Cohen, P. Protein kinases—the major drug targets of the twenty-first century? *Nat. Rev. Drug Disc.* 2002, 1, 309-315.
7. Bridges, A. J. Chemical inhibitors of protein kinases. *Chem. Rev.* 2001, 101(8), 2541-2571.
8. Wang, S.; Meades, C.; Wood, G.; Osnowski, A.; Fischer, P. M. N-(4-(4-methylthiazol-5-yl) pyrimidin-2-yl)-N-phenylamines as antiproliferative compounds. PCT Intl. Patent Appl. Publ. WO 2003029248; Cyclacel Limited, UK.
9. Wu, S. Y.; McNae, I.; Kontopidis, G.; McClue, S. J.; McInnes, C. et al. Discovery of a Novel Family of CDK Inhibitors with the Program LIDAEUS: Structural Basis for Ligand-Induced Disordering of the Activation Loop. *Structure* 2003, 11, 399-410.
10. Fischer, P. M.; Wang, S.; Wood, G. Inhibitors of cyclin dependent kinases as anti-cancer agent. PCT Intl. Patent Appl. Publ. WO 02/079193; Cyclacel Limited, UK.
11. Wang, S.; Fischer, P. M. Anti-cancer compounds. US Patent Appl. Publ. 2002/0019404.
12. Fischer, P. M.; Wang, S. 2-substituted 4-heteroaryl-pyrimidines and their use in the treatment of proliferative disorders. PCT Intl. Patent Appl. Publ. WO 2001072745; Cyclacel Limited, UK.
13. Knockaert, M.; Greengard, P.; Meijer, L. Pharmacological inhibitors of cyclin-dependent kinases. *Trends Pharmacol. Sci.* 2002, 23, 417-425.
14. Fischer, P. M.; Endicott, J.; Meijer, L. Cyclin-dependent kinase inhibitors. *Progress in Cell Cycle Research;* Editions de la Station Biologique de Roscoff: Roscoff, France, 2003; pp 235-248.
15. Fravolini, A.; Grandolini, G.; Martani, A. New heterocyclic ring systems from α-hydroxymethylene ketones. V. Reaction of 2-methyl-6-hydroxymethylene-4,5,6,7-tetrahydrobenzothiazol-7-one with amines and amidines. *Gazz. Chim. Ital.* 1973, 103, 1063-1071.
16. Cleaver, L.; Croft, J. A.; Ritchie, E.; Taylor, W. C. Chemical studies of the Proteaceae. IX. Synthesis of 5-alkylresorcinols from aliphatic precursors. *Aust. J. Chem.* 1976, 29, 1989-2001.
17. Fadda, A. A.; El-Houssini, M. S. Synthesis of cyclic ketones by activated nitriles. *J. Ind. Chem. Soc.* 1990, 67, 915-917.
18. Kost, A. N.; Ovseneva, L. G. Synthesis of 4-substituted dihydroresorcinols. *Zh. Obshch. Khim.* 1962, 32, 3983-3986.
19. Lehmann, G.; Luecke, B.; Schick, H.; Hilgetag, G. 2-Substituted 7-oxo-4,5,6,7-tetrahydrobenzothiazoles. *Z. Chem.* 1967, 7, 422.
20. Bell, R. P.; Davis, G. G. Kinetics of the bromination of some enols and their anions. *J. Chem. Soc* 1965, 353-361.
21. Fravolini, A.; Grandolini, G.; Martani, A. New heterocyclic ring systems from α-hydroxymethylene ketones. III. Pyrazolobenzothiazoles and thiazolo-benzoisoxazoles. *Gazz. Chim. Ital.* 1973, 103, 755-769.
22. Bredereck, H.; Effenberger, F.; Botsch, H. Acid amide reactions. XLV. Reactivity of formamidines, dimethylformamide diethyl acetal (amide acetal), and bis(dimethylamino)methoxymethane (aminal ester). *Chem. Ber.* 1964, 97, 3397-3406.
23. Wang D, De la Fuente C, Deng L, Wang L, Zilberman I, Eadie C, Healey M, Stein D, Denny T, Harrison L E, Meijer L, Kashanchi F. Inhibition of human immunodeficiency virus type 1 transcription by chemical cyclin-dependent kinase inhibitors. *J. Virol.* 2001; 75: 7266-7279.
24. Chen, Y. H.; Hansen, L.; Chen, M. X.; Bjorbaek, C.; Vestergaard, H.; Hansen, T.; Cohen, P. T.; Pedersen, O. *Diabetes,* 1994, 43, 1234.
25. Nikoulina, S. E.; Ciaraldi, T. P.; Mudaliar, S.; Mohideen, P.; Carter, L.; Henry, R. R. *Diabetes,* 2000, 49, 263.
26. Goedert, M. *Curr. Opin. Gen. Dev.,* 2001, 11, 343.
27. Mattson, M. P. *Nat. Rev. Mol. Cell. Biol.,* 2000, 1, 120.
28. Zhu, A. J.; Watt, F. M. *Development,* 1999, 126, 2285.
29. DasGupta, R.; Fuchs, E. *Development,* 1999, 126, 4557.
30. Sunkel et al., *J. Cell Sci.,* 1988, 89, 25.
31. Llamazares et al., *Genes Dev.,* 1991, 5, 2153.
32. Glover et al., *Genes Dev.,* 1998, 12, 3777.
33. Lee et al., *Proc. Natl. Acad. Sci. USA,* 1998, 95, 9301.
34. Leung et al., *Nat. Struct. Biol.,* 2002, 9, 719.
35. Kauselmann et al., *EMBO J.,* 1999, 18, 5528.
36. Nigg, *Curr. Opin. Cell Biol.,* 1998, 10, 776.
37. Yuan et al., *Cancer Res.,* 2002, 62, 4186.
38. Seong et al., *J. Biol. Chem.,* 2002, 277, 32282.
39. Lane et al., *J. Cell. Biol.,* 1996, 135, 1701.
40. Cogswell et al., *Cell Growth Differ.,* 2000, 11, 615.
41. Liu et al., *Proc. Natl. Acad. Sci. USA,* 2002, 99, 8672.
42. Toyoshima-Morimoto et al., *Nature,* 2001, 410, 215.
43. Roshak et al., *Cell. Signalling,* 2000, 12, 405.
44. Smits et al., *Nat. Cell Biol.,* 2000, 2, 672.
45. van Vugt et al., *J. Biol. Chem.,* 2001, 276, 41656.
46. Sumara et al., *Mol. Cell,* 2002, 9, 515.
47. Golan et al., *J. Biol. Chem.,* 2002, 277, 15552.
48. Kotani et al., *Mol. Cell,* 1998, 1, 371.
49. Feng et al., *Cell Growth Differ.,* 2001, 12, 29.
50. Dai et al., *Oncogene,* 2002, 21, 6195.
51. Nurse, *Nature,* 1990, 344, 503.
52. Nigg, *Nat. Rev. Mol. Cell Biol.,* 2001, 2, 21.
53. Hagting et al., *EMBO J.,* 1998, 17, 4127.

54. Hagting et al., *Curr. Biol.,* 1999, 9, 680.
55. Yang et al., *J. Biol. Chem.,* 2001, 276, 3604.
56. Takizawa et al., *Curr. Opin. Cell Biol.,* 2000, 12, 658.
57. Seki et al., *Mol. Biol. Cell,* 1992, 3, 1373.
58. Heald et al., *Cell,* 1993, 74, 463.
59. Dalal et al., *Mol. Cell. Biol.,* 1999, 19, 4465.
60. Toyoshima-Morimoto et al., *Nature,* 2001, 410, 215.
61. Toyoshima-Morimoto et al., *EMBO Rep.,* 2002, 3, 341.
62. Wang et al., *Mol Cell. Biol.,* 2002, 22, 3450.
63. Yin, J.; Zhao, M. M.; Huffman, M. A.; McNamara, J. M. *Org. Lett.* 2002, 4, 3481.

TABLE 1

Summary of biological activity.

| | Kinase inhibition IC$_{50}$ (µM) at [ATP] = 100 µM | | | | | | 72-h MTT IC$_{50}$ (µM) | | | |
|---|---|---|---|---|---|---|---|---|---|---|
| Cpd | Cyclin B - CDK1 | Cyclin A - CDK2 | Cyclin E - CDK2 | Cyclin D1 - CDK4 | Cyclin H - CDK7 | Cyclin T - CDK9 | GSK-3 | A549 | HT29 | Saos-2 |
| 1 | 1.0 ± 0.2 | 0.56 ± 0.04 | 0.05 ± 0.04 | 3.8 ± 0.6 | 1.7 ± 0.5 | 0.008 | n/d | 0.68 ± 0.23 | 1.4 ± 0.3 | 1.2 ± 0.7 |
| 2 | 2.8 ± 0.7 | 4.2 ± 0.9 | 0.4 ± 0.1 | 9.2 ± 1.3 | >100 | 6.1 | n/d | 2.8 ± 1.0 | 7.1 ± 1.3 | 4.4 ± 1.8 |
| 3 | 1.1 ± 0.4 | 0.002 ± 0.001 | 0.02 ± 0.01 | 1.1 ± 0.7 | 0.11 ± 0.03 | 0.013 ± 0.006 | 1.5 ± 0.9 | 2.5 ± 1.2 | 9.4 ± 5.6 | 2.3 ± 1.8 |
| 5 | 0.60 ± 0.12 | 0.009 ± 0.003 | 0.002 ± 0.001 | 1.0 ± 0.001 | 0.64 ± 0.23 | 1.6 ± 0.8 | 20 ± 4 | 4.2 ± 1.2 | 9.9 ± 1.2 | 6.6 ± 5.8 |
| 6 | 7.5 ± 6.3 | 0.058 ± 0.007 | 0.021 ± 0.001 | 0.07 ± 0.02 | 0.13 ± 0.03 | 2.1 ± 0.7 | 14 ± 2 | 8.0 ± 4.0 | 3.6 ± 1.0 | 5.3 ± 1.9 |
| 4 | 45 ± 25 | 0.91 ± 0.59 | 0.4 ± 0.1 | >100 | 2.2 ± 0.5 | 0.52 ± 0.06 | >100 | 3.5 ± 1.4 | 2.1 ± 2.0 | 5.0 ± 0.8 |
| 8 | 0.23 ± 0.19 | 0.014 ± 0.012 | 0.089 ± 0.016 | 0.22 ± 0.19 | 2.3 ± 0.4 | 3.3 ± 1.6 | 1.2 ± 0.5 | 6.0 ± 5.1 | 4.7 ± 3.8 | 5.0 ± 2.7 |
| 7 | 0.058 ± 0.046 | 0.014 ± 0.006 | 0.049 ± 0.002 | 0.075 ± 0.054 | 2.8 ± 0.6 | 4.1 ± 1.7 | 0.64 ± 0.49 | 3.3 ± 0.3 | 4.0 ± 0.1 | 4.9 ± 3.4 |
| 10 | 22 ± 8 | 47 ± 20 | 3.2 ± 0.8 | >40 | 44 ± 11 | >100 | 5.9 ± 0.8 | >40 | >40 | >40 |
| 9 | 8 ± 2 | 14 ± 6 | 1.18 ± 0.03 | >80 | 3.9 ± 1.4 | 39 ± 19 | 3.1 ± 0.1 | >20 | >20 | >20 |
| 11 | 2.2 ± 0.7 | 1.7 | 0.001 ± 0.001 | 1.68 ± 0.04 | >20 | n/d | n/d | n/d | n/d | n/d |
| 12 | 5.2 ± 1.3 | 4.3 ± 2.5 | 0.048 ± 0.013 | 5 ± 4 | >20 | n/d | n/d | n/d | n/d | n/d |
| 13 | 1.9 ± 0.7 | 0.92 ± 0.47 | 0.0007 ± 0.0003 | 0.61 ± 0.09 | 2.5 ± 1.0 | 0.36 ± 0.14 | 2.9 ± 0.3 | n/d | n/d | n/d |
| 14 | 0.054 ± 0.016 | 0.022 ± 0.010 | 0.001 ± 0.001 | 0.25 ± 0.12 | n/t | n/d | 0.17 ± 0.07 | n/d | n/d | n/d |

TABLE 2

Selected compounds of the invention

| Cpd No. | Structure | | Name |
|---|---|---|---|
| 1 | (2-Methyl-4,5-dihydro-thiazolo[4,5-h]quinazolin-8-yl)-(3-nitro-phenyl)-amine | | 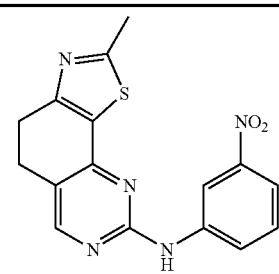 |
| 2 | (2-Methyl-4,5-dihydro-thiazolo[4,5-h]quinazolin-8-yl)-(4-trifluoromethyl-phenyl)-amine | | 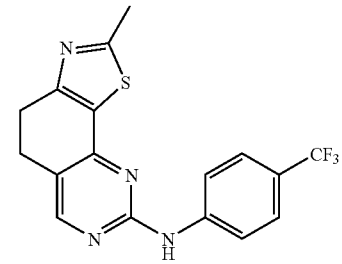 |

TABLE 2-continued

Selected compounds of the invention

| Cpd No. | Structure | Name |
|---|---|---|
| 3 | 3-(2-Methyl-4,5-dihydro-thiazolo[4,5-h]quinazolin-8-ylamino)-phenol | |
| 4 | (2-Methyl-4,5-dihydro-thiazolo[4,5-h]quinazolin-8-yl)-(4-morpholin-4-yl-phenyl)-amine | |
| 5 | 4-(2-Methyl-4,5-dihydro-thiazolo[4,5-h]quinazolin-8-ylamino)-phenol | |
| 6 | N,N-Dimethyl-N'-(2-methyl-4,5-dihydro-thiazolo[4,5-h]quinazolin-8-yl)-benzene-1,4-diamine | |
| 7 | (6-Chloro-pyridin-3-yl)-(2-methyl-4,5-dihydro-thiazolo[4,5-h]quinazolin-8-yl)-amine | |

TABLE 2-continued

Selected compounds of the invention

| Cpd No. | Structure | Name |
| --- | --- | --- |
| 8 | (6-Methoxy-pyridin-3-yl)-(2-methyl-4,5-di-hydro-thiazolo[4,5-h]quinazolin-8-yl)-amine | 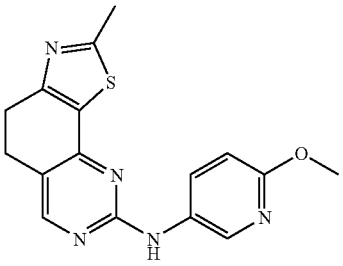 |
| 9 | Methyl-(2-methyl-4,5-dihydro-thiazolo[4,5-h]quinazolin-8-yl)-(3-nitro-phenyl)-amine | 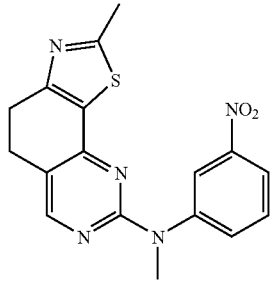 |
| 10 | Methyl-(2-methyl-thiazolo[4,5-h]quinazolin-8-yl)-(3-nitro-phenyl)-amine | 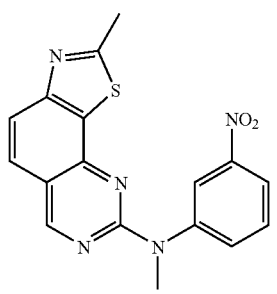 |
| 11 | (2-Methyl-4,5-dihydro-thiazolo[4,5-h]quinazolin-8-yl)-phenyl-amine | 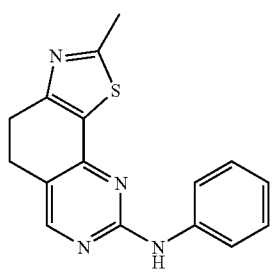 |
| 12 | (2-Methyl-thiazolo[4,5-h]quinazolin-8-yl)-phenyl-amine | 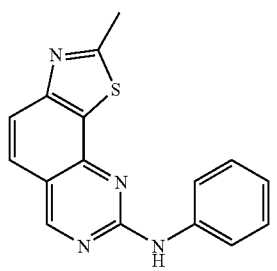 |

TABLE 2-continued

Selected compounds of the invention

| Cpd No. | Structure | Name |
|---|---|---|
| 13 | $N^8$-Phenyl-4,5-dihydro-thiazolo[4,5-h]quinazoline-2,8-diamine | |
| 14 | $N^8$-(3-Nitro-phenyl)-4,5-dihydro-thiazolo[4,5-h]quinazoline-2,8-diamine | |
| 15 | 2-Methyl-4,5-dihydro-thiazolo[4,5-h]quinazolin-8-ylamine | |
| 16 | N-(2-Methyl-4,5-dihydro-thiazolo[4,5-h]quinazolin-8-yl)-benzamide | |
| 17 | Benzyl-(2-methyl-4,5-dihydro-thiazolo[4,5-h]quinazolin-8-yl)-amine | |

TABLE 2-continued

Selected compounds of the invention

| Cpd No. | Structure | Name |
|---|---|---|
| 18 | 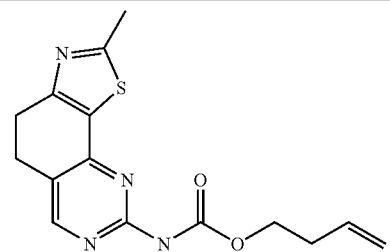 | (2-Methyl-4,5-dihydro-thiazolo[4,5-h]quinazolin-8-yl)-carbamic acid but-3-enyl ester |
| 19 | 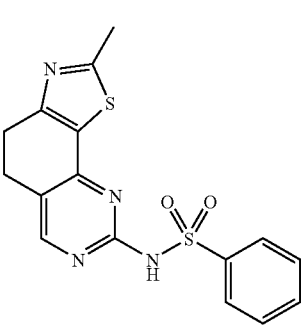 | N-(2-Methyl-4,5-dihydro-thiazolo[4,5-h]quinazolin-8-yl)-benzenesulfonamide |

The invention claimed is:

1. A compound of formula 1, or a pharmaceutically acceptable salt thereof,
wherein:

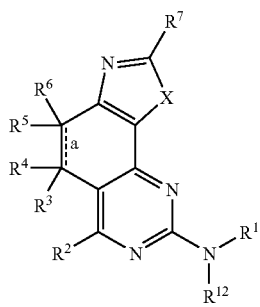

X is S;
"a" is a single bond; or
"a" is a double bond and one of $R^3$ and $R^4$, and one of $R^5$ and $R^6$ are absent;
$R^1$ is H; or is selected from an alkyl group, a cycloalkyl group, a heteroaryl group, an aralkyl group, CO-alkyl, $SO_2$-alkyl, $CO_2R^{13}$ and an aryl group, each of which optionally contains one or more heteroatoms, and is optionally substituted with one or more groups selected from $R^8$ and $R^9$;
$R^2$ is H, $R^8$, or an alkyl group optionally substituted with one or more $R^8$ groups;
$R^3$, $R^4$, $R^5$, and $R^6$ are each independently selected from H, $R^8$, an alkyl group and an alkenyl group, wherein said alkyl and alkenyl groups are optionally substituted with one or more $R^8$ groups; or
$R^3$ and $R^4$, and/or $R^5$ and $R^6$ together represent =O;

$R^7$ is H, $R^8$, $NH(CH_2)_nR^9$, $CO(CH_2)_nR^9$, $NHCO(CH_2)_nR^9$, $O(CH_2)_nR^9$, or an alkyl or phenyl group, each of which is optionally substituted with one or more groups selected from $R^8$ and $R^9$;
$R^8$ is $OR^{10}$, $NR^{10}R^{11}$, halogen, $CF_3$, $NO_2$, $COR^{10}$, CN, $COOR^{10}$, $CONR^{10}R^{11}$, $SO_2R^{10}$ or $SO_2NR^{10}R^{11}$;
$R^9$ is a saturated or unsaturated 5- or 6-membered cyclic group optionally containing one or more heteroatoms selected from N, O and S, and optionally substituted with one or more $R^8$ groups;
$R^{10}$, $R^{11}$, $R^{12}$ and $R^{13}$ are each independently H or a hydrocarbyl group; and
n is 0, 1, 2 or 3.

2. The compound according to claim 1, wherein:
$R^{10}$ and $R^{11}$ are each independently H or alkyl; and
$R^{13}$ is alkyl or alkenyl.

3. The compound according to claim 1, wherein:
$R^1$ is H; or is selected from $CO_2R^{13}$, a $C_1$-$C_{12}$ alkyl group, a $C_3$-$C_{12}$ cycloalkyl group, a $C_6$-$C_{12}$ aryl group, or a $C_{3-12}$ heteroaryl group, a ($C_1$-$C_{12}$ alkyl)-($C_6$-$C_{12}$ aryl) group, $SO_2$—($C_6$-$C_{12}$ aryl) and CO—($C_6$-$C_{12}$ aryl), wherein said alkyl, cycloalkyl, heteroaryl and aryl group optionally contains one, two or three heteroatoms selected from N, O, or S, and is optionally substituted with one, two or three groups selected from $R^8$ and $R^9$;
$R^2$ is H, $R^8$, or a $C_1$-$C_3$ alkyl group optionally substituted with one or more $R^8$ groups;
$R^3$, $R^4$, $R^5$, and $R^6$ are each independently selected from H, $R^8$, a $C_1$-$C_3$ alkyl group optionally substituted with one or more $R^8$ groups, and a $C_2$-$C_3$ alkenyl group optionally substituted with one or more $R^8$ groups;
$R^7$ is H, $R^8$, phenyl, $NH(CH_2)_nR^9$, $CO(CH_2)_nR^9$, NHCO$(CH_2)_nR^9$, $O(CH_2)_nR^9$, or a $C_1$-$C_6$ alkyl group optionally substituted with one or more groups selected from $R^8$ and $R^9$.

4. The compound according to claim 1, wherein:
$R^1$ is H; or is selected from phenyl, pyridin-2-yl, pyridin-3-yl, CO-phenyl, $CH_2$-phenyl, $SO_2$-phenyl, $CO_2$-alkyl and $CO_2$-alkenyl, each of which may be optionally substituted by one or more substituents selected from $R^8$ and $R^9$;
$R^2$, $R^3$, $R^4$, $R^5$, and $R^6$ are each independently H or $C_{1-3}$ alkyl optionally substituted by one or more hydroxy groups; and
$R^7$ is $C_{1-6}$ alkyl or $R^8$;
$R^8$ is OH, OMe, OEt, $O^iPr$, $NH_2$, NHMe, $NMe_2$, NHEt, $NH^iPr$, $CF_3$, F, Cl, Br, I, $NO_2$, COMe, COEt, $CO^iPr$, CN, COOH, COOMe, $CONH_2$, CONHMe, $CONMe_2$, $SO_2Me$ or $SO_2NH_2$.

5. The compound according to claim 1, wherein:
$R^8$ is OH, OMe, OEt, $O^iPr$, $NH_2$, NHMe, $NMe_2$, NHEt, $NH^iPr$, $CF_3$ or $NO_2$; and
$R^9$ is morpholino.

6. The compound according to claim 1, wherein:
$R^1$ is H; or is selected from a phenyl group, CO-phenyl, $SO_2$-phenyl, $CH_2$-phenyl and $CO_2$—$CH_2$ $CH_2CH=CH$, each of which may be optionally substituted by one or more substituents selected from $NO_2$, $CF_3$, OH, morpholino and $NMe_2$;
$R^2$ is H;
$R^3$, $R^4$, $R^5$, and $R^6$ are each independently selected from H, $CH_3$, $CH_2OH$ and $CH_2CH_2OH$; and
$R^7$ is selected from $CH_3$, $NH_2$, $NHCH_3$, $OCH_3$ and $OCH_2CH_3$.

7. The compound according to claim 1, wherein:
$R^1$ is H; or is a phenyl group optionally substituted in the 3- or 4-position by a substituent selected from $NO_2$, $CF_3$, OH, morpholino and $NMe_2$; or $R^1$ is CO-phenyl, $CH_2$-phenyl, $SO_2$-phenyl, or $CO_2$—$CH_2CH_2CH=CH$;
$R^2$ is H;
$R^3$, $R^4$, $R^5$, and $R^6$ are all H; and
$R^7$ is $NH_2$ or $CH_3$.

8. The compound according to claim 1, which is selected from the following:
(2-Methyl-4,5-dihydro-thiazolo[4,5-h]quinazolin-8-yl)-(3-nitro-phenyl)-amine;
(2-Methyl-4,5-dihydro-thiazolo[4,5-h]quinazolin-8-yl)-(4-trifluoromethyl-phenyl)-amine;
3-(2-Methyl-4,5-dihydro-thiazolo[4,5-h]quinazolin-8-ylamino)-phenol;
(2-Methyl-4,5-dihydro-thiazolo[4,5-h]quinazolin-8-yl)-(4-morpholin-4-yl-phenyl)-amine;
4-(2-Methyl-4,5-dihydro-thiazolo[4,5-h]quinazolin-8-ylamino)-phenol;
N,N-Dimethyl-N'-(2-methyl-4,5-dihydro-thiazolo[4,5-h]quinazolin-8-yl)-benzene-1,4-diamine;
(6-Chloro-pyridin-3-yl)-(2-methyl-4,5-dihydro-thiazolo[4,5-h]quinazolin-8-yl)-amine;
(6-Methoxy-pyridin-3-yl)-(2-methyl-4,5-dihydro-thiazolo[4,5-h]quinazolin-8-yl)-amine;
Methyl-(2-methyl-4,5-dihydro-thiazolo[4,5-h]quinazolin-8-yl)-(3-nitro-phenyl)-amine;
Methyl-(2-methyl-thiazolo[4,5-h]quinazolin-8-yl)-(3-nitro-phenyl)-amine;
(2-Methyl-4,5-dihydro-thiazolo[4,5-h]quinazolin-8-yl)-phenyl-amine;
(2-Methyl-thiazolo[4,5-h]quinazolin-8-yl)-phenyl-amine;
$N^8$-Phenyl-4,5-dihydro-thiazolo[4,5-h]quinazoline-2,8-diamine;
$N^8$-(3-Nitro-phenyl)-4,5-dihydro-thiazolo[4,5-h]quinazoline-2,8-diamine;
2-Methyl-4,5-dihydro-thiazolo[4,5-h]quinazolin-8-ylamine;
N-(2-Methyl-4,5-dihydro-thiazolo[4,5-h]quinazolin-8-yl)-benzamide;
Benzyl-(2-methyl-4,5-dihydro-thiazolo[4,5-h]quinazolin-8-yl)-amine;
(2-Methyl-4,5-dihydro-thiazolo[4,5-h]quinazolin-8-yl)-carbamic acid but-3-enyl ester;and
N-(2-Methyl-4,5-dihydro-thiazolo[4,5-h]quinazolin-8-yl)-benzenesulfonamide.

9. The compound according to claim 1, which is selected from the following:
(2-Methyl-4,5-dihydro-thiazolo[4,5-h]quinazolin-8-yl)-(3-nitro-phenyl)-amine;
(2-Methyl-4,5-dihydro-thiazolo[4,5-h]quinazolin-8-yl)-(4-trifluoromethyl-phenyl)-amine;
3-(2-Methyl-4,5-dihydro-thiazolo[4,5-h]quinazolin-8-ylamino)-phenol;
(2-Methyl-4,5-dihydro-thiazolo[4,5-h]quinazolin-8-yl)-(4-morpholin-4-yl-phenyl)-amine;
4-(2-Methyl-4,5-dihydro-thiazolo[4,5-h]quinazolin-8-ylamino)-phenol;
N,N-Dimethyl-N'-(2-methyl-4,5-dihydro-thiazolo[4,5-h]quinazolin-8-yl)-benzene-1,4-diamine;
(2-Methyl-4,5-dihydro-thiazolo[4,5-h]quinazolin-8-yl)-(4-morpholin-4-yl-phenyl)-amine;
(6-Methoxy-pyridin-3-yl)-(2-methyl-4,5-dihydro-thiazolo[4,5-h]quinazolin-8-yl)-amine;
(6-Chloro-pyridin-3-yl)-(2-methyl-4,5-dihydro-thiazolo[4,5-h]quinazolin-8-yl)-amine;
Methyl-(2-methyl-4,5-dihydro-thiazolo[4,5-h]quinazolin-8-yl)-(3-nitro-phenyl)-amine;
(2-Methyl-4,5-dihydro-thiazolo[4,5-h]quinazolin-8-yl)-phenyl-amine;
(2-Methyl-thiazolo[4,5-h]quinazolin-8-yl)-phenyl-amine;
$N^8$-Phenyl-4,5-dihydro-thiazolo[4,5-h]quinazoline-2,8-diamine; and
$N^8$-(3-Nitro-phenyl)-4,5-dihydro-thiazolo[4,5-h]quinazoline-2,8-diamine.

10. A pharmaceutical composition comprising a compound of formula 1 or a pharmaceutically acceptable salt thereof, admixed with a pharmaceutically acceptable diluent, excipient or carrier, wherein said compound of formula 1 is:

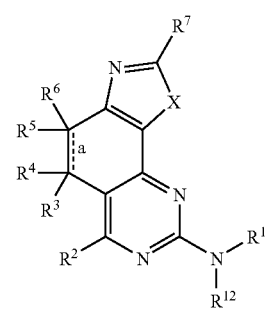

1

X is S;
"a" is a single bond; or
"a" is a double bond and one of $R^3$ and $R^4$, and one of $R^5$ and $R^6$ are absent;
$R^1$ is H; or is selected from an alkyl group, a cycloalkyl group, a heteroaryl group, an aralkyl group, CO-alkyl, $SO_2$-alkyl, $CO_2R^{13}$ and an aryl group, each of which optionally contains one or more heteroatoms, and is optionally substituted with one or more groups selected from $R^8$ and $R^9$;

$R^2$ is H, $R^8$, or an alkyl group optionally substituted with one or more $R^8$ groups;

$R^3$, $R^4$, $R^5$, and $R^6$ are each independently selected from H, $R^8$, an alkyl group and an alkenyl group, wherein said alkyl and alkenyl groups are optionally substituted with one or more $R^8$ groups; or $R^3$ and $R^4$, and/or $R^5$ and $R^6$ together represent =O;

$R^7$ is H, $R^8$, $NH(CH_2)_nR^9$, $CO(CH_2)_nR^9$, $NHCO(CH_2)_nR^9$, $O(CH_2)_nR^9$, or an alkyl or phenyl group, each of which is optionally substituted with one or more groups selected from $R^8$ and $R^9$;

$R^8$ is $OR^{10}$, $NR^{10}R^{11}$, halogen, $CF_3$, $NO_2$, $COR^{10}$, CN, $COOR^{10}$, $CONR^{10}R^{11}$, $SO_2R^{10}$ or $SO_2NR^{10}R^{11}$;

$R^9$ is a saturated or unsaturated 5- or 6-membered cyclic group optionally containing one or more heteroatoms selected from N, O and S, and optionally substituted with one or more $R^8$ groups;

$R^{10}$, $R^{11}$, $R^{12}$ and $R^{13}$ are each independently H or a hydrocarbyl group; and n is 0, 1, 2 or 3.

11. A method for treating a cancer selected from the group consisting of lung cancer, colon cancer andosteosarcoma, comprising administering to a subject in need thereof, a compound of claim 1, or a pharmaceutically acceptable salt thereof, in an amount sufficient to treat the subeject for said cancer.

12. A method of treating a viral disorder, comprising administering to a subject in need thereof, a compound of claim 1, or a pharmaceutically acceptable salt thereof, in an amount sufficient to treat said subject for the viral disorder, wherein the viral disorder is selected from human cytomegalovirus (HCMV), herpes simplex virus type 1 (HSV-1), human immunodeficiency virus type 1 (HIV-1), and varicella zoster virus (VZV).

13. A method of treating a cancer selected from the group consisting of lung cancer, colon cancer and osteosarcoma, comprising administering to a subject in need thereof, a compound of claim 1, or a pharmaceutically acceptable salt thereof, in an amount sufficient to inhibit at least one CDK enzyme and treat the subject for the cancer.

14. The method according to claim 13, wherein the CDK enzyme is CDK1, CDK2, CDK3, CDK4, CDK6, CDK7, CDK8 and/or CDK9.

15. A process for preparing a compound of formula 1 as defined in claim 1, said process comprising the steps of:

(i) reacting a compound of formula 7 with a compound of formula 8 to form a compound of formula 9

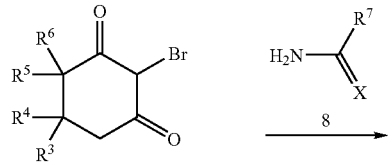

-continued

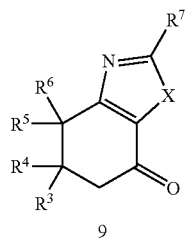

9

(ii) converting said compound of formula 9 into a compound of formula 1 which further comprises the steps of:

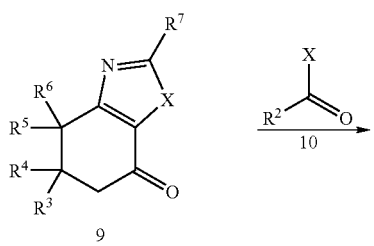

9

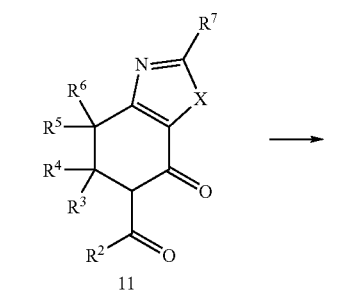

11

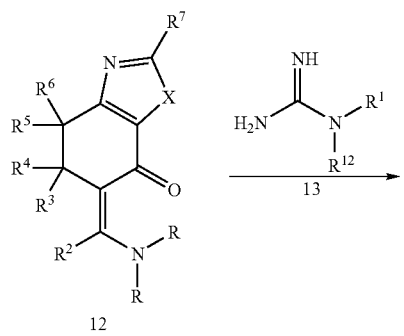

12

1a (iii) reacting said compound of formula 9 with a compound of formula 10 to form a compound of formula 11;
(iv) converting said compound of formula 11 into a compound of formula 12;
(v) reacting said compound of formula 12 with a compound of formula 13 to form a compound of formula 1a; and
(vi) optionally, oxidising said compound of formula 1a to form a compound of formula 14

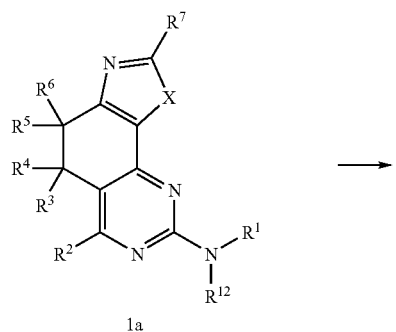

1a

⟶

-continued

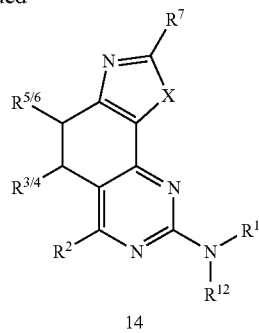

14

16. The method of claim 15, wherein said method does not comprise oxidizing said compound of formula Ia to form a compound of formula 14.

17. The method of claim 15, wherein said method comprises oxidizing said compound of formula Ia to form a compound of formula 14.

* * * * *